United States Patent [19]
Saito et al.

[11] Patent Number: 6,162,798
[45] Date of Patent: *Dec. 19, 2000

[54] INHIBITOR OF ATHEROSCLEROTIC INTIMAL THICKENING

[75] Inventors: Yasushi Saito, Chiba; Masaki Kitahara, Shiraoka-machi; Mitsuaki Sakashita, Shiraoka-machi; Kyomi Toyoda, Shiraoka-machi; Toshie Shibazaki, Shiraoka-machi, all of Japan

[73] Assignees: Nissan Chemical Industries Ltd., Tokyo; Kowa Company, Ltd., Nagoya, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 07/953,716

[22] Filed: Sep. 30, 1992

[30] Foreign Application Priority Data

Oct. 4, 1991 [JP] Japan ................................. 3-257870

[51] Int. Cl.[7] ..................... A61K 31/695; A61K 31/44
[52] U.S. Cl. ..................... 514/63; 514/290; 514/301; 514/303; 514/824
[58] Field of Search ..................... 546/101, 173, 546/174, 175, 178; 514/290, 215, 217, 258, 301, 63, 278, 303, 824

[56] References Cited

U.S. PATENT DOCUMENTS

| | | | |
|---|---|---|---|
| 4,761,419 | 8/1988 | Picard et al. | 514/311 |
| 4,822,799 | 4/1989 | Kathawala | 514/303 |
| 5,011,930 | 4/1991 | Fujikawa et al. | 546/101 |
| 5,024,999 | 6/1991 | Fujikawa et al. | 514/303 |
| 5,026,698 | 6/1991 | Fujikawa et al. | 514/301 |

FOREIGN PATENT DOCUMENTS

| | | |
|---|---|---|
| 0 304 063 | 2/1989 | European Pat. Off. . |
| 0 304 063 A2 | 2/1989 | European Pat. Off. . |
| 0304 063 | 2/1989 | European Pat. Off. . |
| 0 339 358 | 11/1989 | European Pat. Off. . |
| 0 339 358 A1 | 11/1989 | European Pat. Off. . |
| 0339 358 | 11/1989 | European Pat. Off. . |
| 0 367 235 | 5/1990 | European Pat. Off. . |
| 0 367 235 A1 | 5/1990 | European Pat. Off. . |
| 0367 235 | 5/1990 | European Pat. Off. . |

OTHER PUBLICATIONS

The Merck Manual of Diagnosis and Therapy, Merck Research Laboratories, 1992, "Generalized Cardiovascular Disorders", pp. 410–411.

D.R. Sliskovic et al, "Inhibitors of Cholesterol Biosynthesis. 4. Trans–6–[2–(Substituted–Quinolinyl)–Ethenyl/Ethyl] Tetrahydro–4–Hydroxy–2H–Pyran–2–Ones, a Novel Series of HMG–CoA Reductase Inhibitors," *J. Med. Chem.*, vol. 34 (1991), pp. 367–373.

New Zealand Patent Office Action, Dated Nov. 24, 1993 (2 Pages) for Patent Application #244555 (New Zealand).

Avery's Drug Treatment, 3rd Edition (1987) Trevor M. Speight ed. pp. 594–595.

Journal of Medicinal Chemistry, vol. 34, No. 1, Jan. 1991, pp. 367–373, D.R. Sliskovic, et al., "Inhibitors of Cholestrol Biosynthesis.4."

Journal of American College of Cardiology, vol. 17, No. 1, Jan. 1991, pp. 251–259, J. Gellman, et al., "Effect of Lovastatin on Intimal Hyperplasia After Balloon Angioplasty: A Study in an Atherosclerotic Hypercholesterolemic Rabbit".

STN File Supplier, AN 91216498, vol. 82, No. 2, Feb. 1991, K. Oogushi, "Preventive Effect of Simvastatin, a Competitive Inhibitor of 3–Hydroxy–3–Methylglutaryl Coenzyme A Reductase, on Coronary Atherosclerosis in Cholesterol–Fed Rabbits".

Pharmacology & Toxicology, vol. 64, No. 2, 1989, pp. 173–176, P. Falke, et al, "Effects of a Competitive Inhibitor (Mevinolin) of 3–Hydroxy–3–Methylglutaryl Coenzyme A Reductase on Human and Bovine Endothelial Cells, Fibroblasts and Smooth Muscle Cells in Vitro".

The Merck Manual of Diagnosis and Therapy, 1987, pp. 386–389, "Generalized Cardiovascular Disorders".

*Primary Examiner*—Raymond Henley, III
*Attorney, Agent, or Firm*—Oblon, Spivak, McClelland, Maier & Neustadt, P.C.

[57] ABSTRACT

An inhibitor of atherosclerotic intimal thickening, which contains an effective amount of a compound of the formula (I):

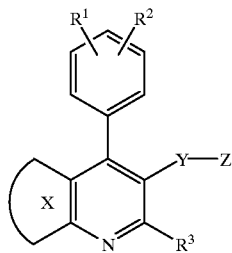

wherein ring X is phenyl, substituted phenyl or 5- or 6-membered heterocyclic aryl and the remaining variables are as defined herein.

14 Claims, No Drawings

INHIBITOR OF ATHEROSCLEROTIC INTIMAL THICKENING

The present invention relates to an inhibitor of atherosclerotic intimal thickening, which contains a pyridine derivative having strong HMG-CoA reductase inhibitory effects and strong inhibitory effects against proliferation of aortic intimal smooth muscle cells (I-SMC) in the atherosclerotic intimal thickening, against migration of aortic medial smooth muscle cells (M-SMC) and against adhesion of blood cells (such as lymphocytes, leukocytes and macrophages) to endothelial cells.

As the onset mechanism, the atherosclerotic intimal thickening of coronary artery is believed to be one of the main causes for myocardial infarction and angina pectoris. This atherosclerotic intimal thickening is considered to be initiated by adhesion of monocytes or platelets to endothelial cells with secretion of cytokines and lipid accumulation and to be progressed by migration of M-SMC from the media to the intima and proliferation of the smooth muscle cells in the intima and increase of extracellular matrix, due to pathological and proliferative activation or modulation of smooth muscle cells. These activation of the cells are promoted by risk factors such as hyperlipidemia. Heretofore, it has been reported that HMG-CoA reductase inhibitors suppress the atherosclerotic intimal thickening by a strong effect to reduce serum cholesterol in an animal model (Biochim. Biophis. Acta, 960, 294–302, (1988)), but the effect in a clinical trial has been found inadequate.

Accordingly, as a more effective inhibitor on atherosclerotic intimal thickening, a drug capable of directly acting on such atherosclerotic lesion, is desired. Heretofore, there have been reports on inhibitory effects on smooth muscle cells by an anti-platelet-derived growth factor (PDGF) drug or an anti-fibroblast growth factor (FGF) drug (Life Science, 28, 1641–1646, (1981); J. Pharm. Exp. Ther., 248, 1167–1174, (1989)), inhibitory effects of calcium antagonists on the migration of smooth muscle cells by PDGF, thromboxane $B_4$ and interluekin-1 (Atherosclerosis, 72, 213–219, (1988)), inhibitory effects of RGD peptides on cell adhesion (J. Cell Biol., 112, 335–344, (1991)), inhibitory effects of a thromboxane synthesis inhibitor on re-athenosis after PTCA (Atherosclerosis, 18, 661–665, (1990)). However, these are the effects of drugs against platelets or stimulation factors such as cytokines, and no drug has been found which directly acts on atherosclerotic pathological smooth muscle cells.

A smooth muscle cell-derived migration factor secreted from smooth muscle cells exhibits stronger stimulation of migration than PDGF and is believed to closely relate to the initiation and progression of atherosclerosis (Atherosclerosis, 72, 213–226, (1991)), but no drug has been found which inhibits such migration of smooth muscle cells. Further, the proliferative character of I-SMC, which can not be suppressed by prostaglandin $I_2$ (Atherosclerosis, 73, 67–69, (1988)), is considered to be an important phenomenon in atherosclerosis. However, no drug has been found which inhibits such proliferative character.

It has been reported that a HMG-CoA reductase inhibitors have an inhibitory effect on cell proliferation in fibroblasts, smooth muscle cells and lymphocytes (J. Biol. Chem., 259, 1546–1551 (1984); ibid 255, 5134–5140; Biochim. Biophys. Acta., 1051, 138–143, (1990)) and also suppress activation of lymphocytes (Int. J. Immunopharmac., 11, 863–869, (1989)). However, such inhibitory effects are not fully satisfactory, and a drug is desired which is more effective and selectively against target cells, particularly against I-SMC, macrophages and monocytes.

The present invention provides an inhibitor of atherosclerotic intimal thickening, which contains an effective amount of a compound of the formula (I):

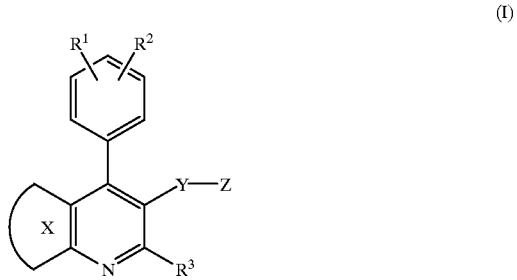

wherein ring X is phenyl, substituted phenyl or 5- or 6-membered heterocyclic aryl;

each of $R^1$ and $R^2$ which are independent of each other, is hydrogen, $C_{1-8}$ alkyl, $C_{3-7}$ cycloalkyl, $C_{1-3}$ alkoxy, n-butoxy, i-butoxy, sec-butoxy, tert-butoxy, $R^{20}R^{21}N$- (wherein each of $R^{20}$ and $R^{21}$ which are independent of each other, is hydrogen or $C_{1-3}$ alkyl), trifluoromethyl, trifluoromethoxy, difluoromethoxy, fluoro, chloro, bromo, phenyl., phenoxy, benzyloxy, hydroxy, trimethylsilyloxy, diphenyl-tert-butylsilyloxy, hydroxymethyl or —O(CH$_2$)$_l$OR$^{22}$ (wherein $R^{22}$ is hydrogen or $C_{1-3}$ alkyl, and l is 1, 2, or 3); or $R^1$ and $R^2$ together form —CH=CH—CH=CH— or methylenedioxy, when they are at the o-position to each other;

$R^3$ is hydrogen, $C_{1-8}$ alkyl, $C_{2-6}$ alkenyl, $C_{3-7}$ cycloalkyl, $C_{5-7}$ cycloalkenyl or

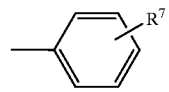

(wherein $R^7$ is hydrogen, $C_{1-8}$ alkyl, $C_{1-8}$ alkoxy, $C_{1-3}$ alkylthio, chloro, bromo, fluoro, chloromethyl, trichloromethyl, trifluoromethyl, trifluoromethoxy, trichloromethoxy, difluoromethoxy, phenoxy, benzyloxy, hydroxy, trimethylsilyloxy, diphenyl-tert-butylsilyloxy or hydroxymethyl); or $C_{1-3}$ alkyl substituted by one

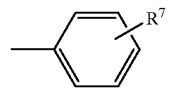

(wherein $R^7$ is as defined above) and zero, one or two $C_{1-3}$ alkyl;

Y is —CH$_2$—, —CH$_2$CH$_2$—, —CH=CH—, —CH$_2$—CH=CH—, —CH=CH—CH$_2$—, —C(CH$_3$)=CH— or —CH=C(CH$_3$)—;

Z is —Q—CH$_2$—W—CH$_2$—CO$_2$R$^{12}$,

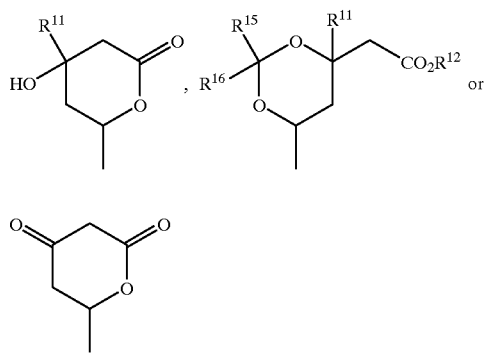

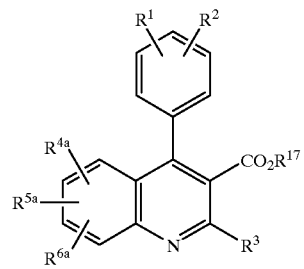

[VIIa]

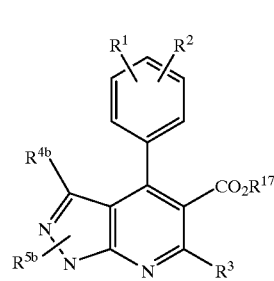

[VIIb]

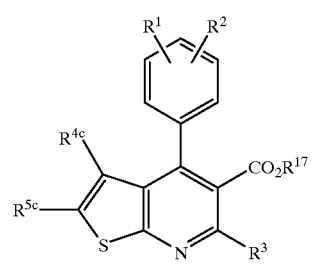

[VIIc]

(wherein Q is —C(O)—, —C(OR$^{13}$)$_2$— or —CH(OH)—,

W is —C(O), —C(OR$^{13}$)$_2$— or —C(R$^{11}$)(OH)—,

R$^{11}$ is hydrogen or C$_{1-3}$ alkyl,

R$^{12}$ is hydrogen, R$^{14}$ (wherein R$^{14}$ is alkyl of a chemically or physiologically hydrolyzable alkyl ester moiety, NHR$^{23}$R$^{24}$R$^{25}$ (wherein each of R$^{23}$, R$^{24}$ and R$^{25}$ is hydrogen or C$_{1-4}$ alkyl), sodium, potassium or ½ calcium), each R$^{13}$ is independently primary or secondary C$_{1-6}$ alkyl, or two R$^{13}$ together form —(CH$_2$)$_2$— or —(CH$_2$)$_3$—, and each of R$^{15}$ and R$^{16}$ which are independent of each other, is hydrogen atom or C$_{1-3}$ alkyl, or R$^{15}$ and R$^{16}$ together form —(CH$_2$)$_2$— or —(CH$_2$)$_3$—.

Such a compound may have at least one or two asymmetric carbon atoms and thus has at least two or more optical isomers. Thus, the compound of the above formula (I) includes all of such optical isomers and mixtures thereof.

Further, among compounds wherein the carboxylic acid derivative moiety (—CO$_2$R$^{12}$) of the substituent Z of the compound of the formula (I) of the present invention is a carboxylic acid derivative moiety other than the one defined by —CO$_2$R$^{12}$, those which are capable of being converted to the carboxylic acid (the compound wherein the —CO$_2$R$^{12}$ moiety is —CO$_2$H) by physiological hydrolysis after intake, are regarded to be equivalent to the compound of the present invention.

The compound of the present invention may be potent inhibitor on adhesion of blood cells (such as monocytes, macrophages), to endothelial cells, and may be suppress the response of early phase for atherosclerotic intimal thickening. Furthermore, they may be able to inhibit migration of aortic medial smooth muscle cells by PDGF and by the conditioned medium of smooth muscle cells (SMC-CM) which may be containing smooth muscle cell-derived migration factor of autocrine stimulation system. Furthermore, the compound of the present invention inhibits $^3$H-thymidine uptake in smooth muscle cells and thus inhibits DNA replication, whereby proliferation of the cells is believed to be effectively inhibited. These effects are more potent in I-SMC than those in M-SMC. From the foregoing, the compound of the present invention is believed to inhibit proliferation of smooth muscle cells in the aortic the intima which is the most important step in the atherosclerotic intimal thickening. On the basis of a discovery that the compound of the present invention has such inhibitory effects against atherosclerotic intimal thickening, the present invention has been accomplished.

The compounds of the present invention i.e. mevalonolactones of the formula (I) can be prepared by the following reactions.

In the reaction formulas, R$^1$, R$^2$, R$^3$, R$^{12}$, R$^{14}$ and ring X are as defined above with respect to the formula (I), and R$^{17}$ is C$_{1-4}$ lower alkyl, such as methyl, ethyl, n-propyl, i-propyl or n-butyl.

Among the compounds of the formula (I), those of the formulas (VIIa), (VIIb) and (VIIc) can be prepared in accordance with the methods disclosed in Japanese Unexamined Patent Publication No. 279866/1989 (corresponding to EP304063 and U.S. Pat. No. 5,011,930), Japanese Unexamined Patent Publication No. 275878/1990 (corresponding to EP339358 and U.S. Pat. No. 5,024,999), and Japanese Unexamined Patent Publication No. 7290/1991 (corresponding to EP367235 and U.S. Pat. No. 5,026,698).

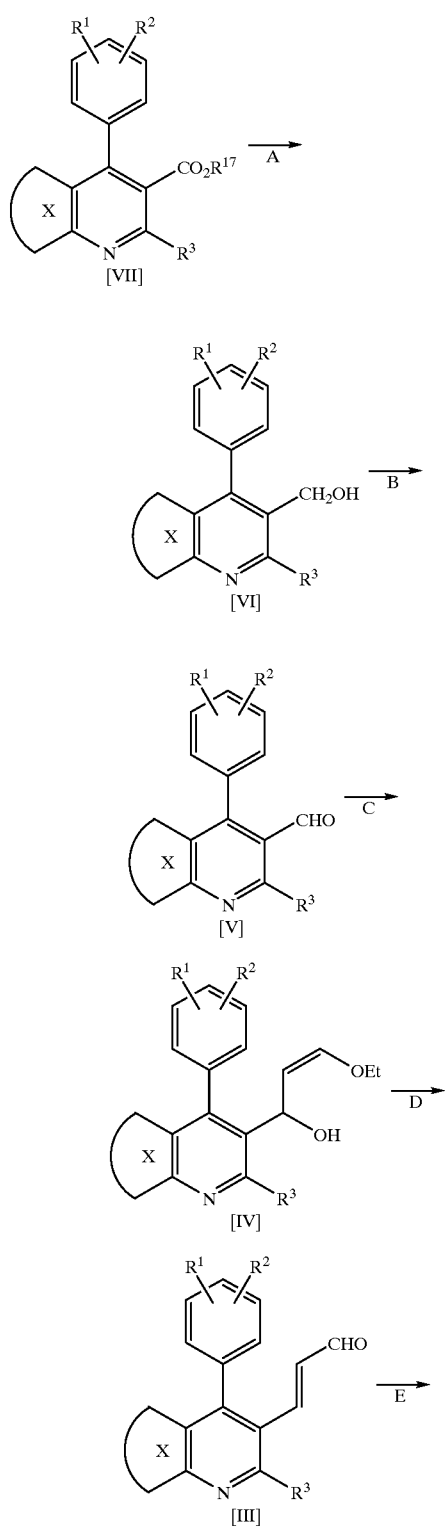
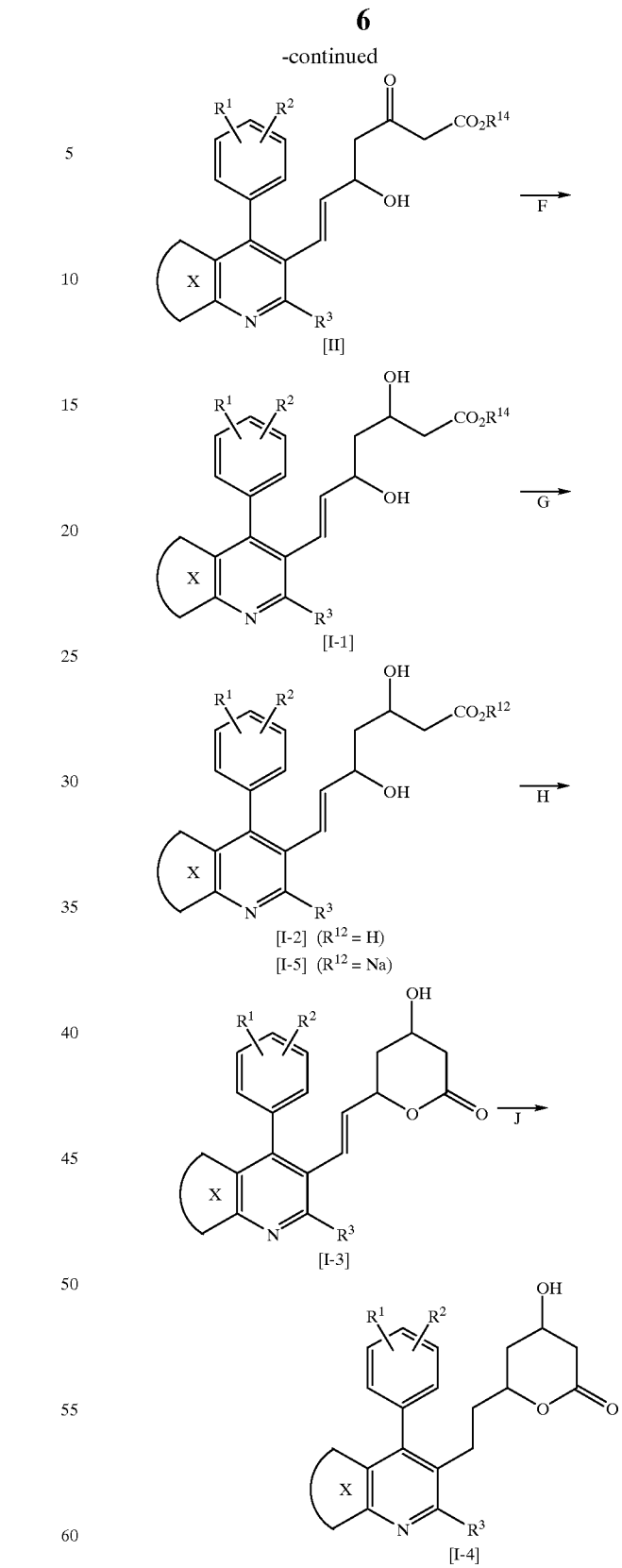

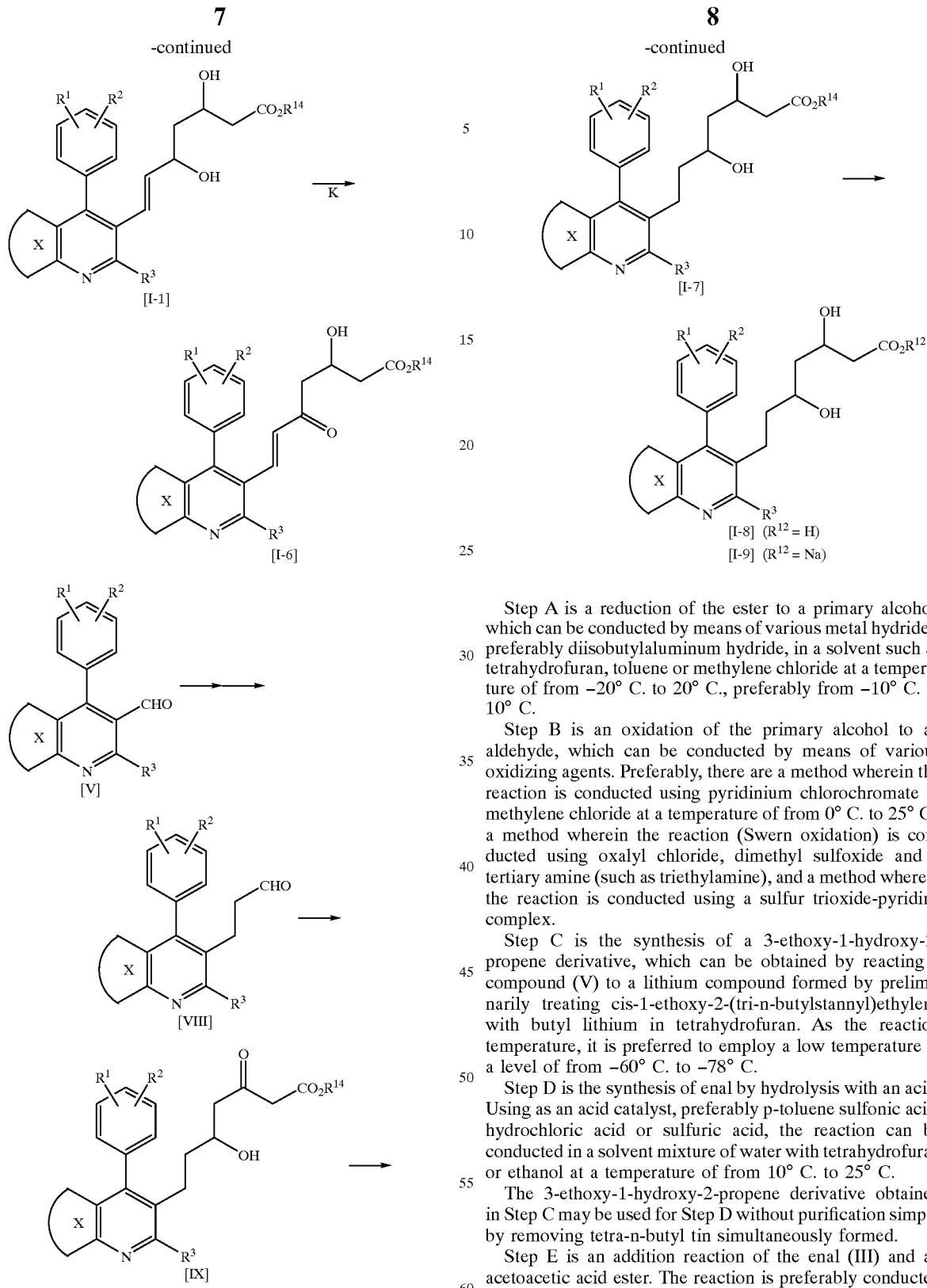

Step A is a reduction of the ester to a primary alcohol, which can be conducted by means of various metal hydrides, preferably diisobutylaluminum hydride, in a solvent such as tetrahydrofuran, toluene or methylene chloride at a temperature of from −20° C. to 20° C., preferably from −10° C. to 10° C.

Step B is an oxidation of the primary alcohol to an aldehyde, which can be conducted by means of various oxidizing agents. Preferably, there are a method wherein the reaction is conducted using pyridinium chlorochromate in methylene chloride at a temperature of from 0° C. to 25° C., a method wherein the reaction (Swern oxidation) is conducted using oxalyl chloride, dimethyl sulfoxide and a tertiary amine (such as triethylamine), and a method wherein the reaction is conducted using a sulfur trioxide-pyridine complex.

Step C is the synthesis of a 3-ethoxy-1-hydroxy-2-propene derivative, which can be obtained by reacting a compound (V) to a lithium compound formed by preliminarily treating cis-1-ethoxy-2-(tri-n-butylstannyl)ethylene with butyl lithium in tetrahydrofuran. As the reaction temperature, it is preferred to employ a low temperature at a level of from −60° C. to −78° C.

Step D is the synthesis of enal by hydrolysis with an acid. Using as an acid catalyst, preferably p-toluene sulfonic acid, hydrochloric acid or sulfuric acid, the reaction can be conducted in a solvent mixture of water with tetrahydrofuran or ethanol at a temperature of from 10° C. to 25° C.

The 3-ethoxy-1-hydroxy-2-propene derivative obtained in Step C may be used for Step D without purification simply by removing tetra-n-butyl tin simultaneously formed.

Step E is an addition reaction of the enal (III) and an acetoacetic acid ester. The reaction is preferably conducted using sodium hydride and n-butyl lithium as the base in tetrahydrofuran at a temperature of from −80° C. to 0° C., preferably from −30° C. to −10° C.

Step F is a reaction wherein the ketocarboxylic acid ester (II) is reduced by various reducing agents.

This is a reaction wherein a carbonyl group is reduced using, for example, sodium borohydride, sodium cyanoborohydride, zinc borohydride, disiamylborane, diborane, tert-butylaminoborane, a pyridine-borane complex, dicyclohexylborane, thexylborane, 9-borabicyclo [3.3.1]nonane, diisopinocamphenyl borane or lithium tri-sec-butylborohydride, to obtain the corresponding dihydroxycarboxylic acid ester (I-1).

This reaction can be conducted in a solvent selected from a hydrocarbon, a halogenated hydrocarbon, a $C_{1-4}$ alcohol, an ether and solvent mixtures thereof at a temperature of from −100° C. to 50° C., preferably from −78° C. to 30° C.

Otherwise, as disclosed in J. Amer. Chem. Soc., 105, 593, (1983), a trialkylborane such as tri-n-butylborane or triethylborane and sodium borohydride may be used at a low temperature.

Further, as disclosed in Tetrahedron Letters, 28, 155, (1987), it is possible to preferentially obtain an erythro product having a biologically stronger activity by using an alkoxydialkylborane such as methoxydiethylborane or ethoxydiethylborane.

This reaction can be conducted using a solvent mixture of a $C_{1-4}$ alcohol and tetrahydrofuran at a temperature of from −80° C. to −50° C., preferably from −72° C. to −68° C.

Step G is a step of hydrolyzing the ester, and the reaction can be conducted using an equimolar amount of a base, preferably potassium hydroxide or sodium hydroxide, in a solvent mixture of water and methanol or ethanol at a temperature of from 10° C. to 25° C.

A free acid obtained here can be reacted with a suitable base to form a salt.

Step H is a step of subjecting the free hydroxy acid (I-2) to a dehydration reaction to form a mevalonolactone, and the reaction can be conducted by refluxing in benzene or toluene while removing the resulting water or by an addition of a suitable dehydrating agent such as a molecular sieve.

Otherwise, the reaction can be conducted using a lactone-forming agent such as a carbodiimide, preferably a water-soluble carbodiimide such as N-cyclohexyl-N'-[2'-(methylmorpholinium)ethyl]carbodiimide p-toluenesulfonate in dry methylene chloride at a temperature of from 10° C. to 35° C., preferably from 20° C. to 25° C.

Step J is a hydrogenation of the double bond connecting the mevalonolactone moiety to the hetero ring, which can be conducted using a catalytic amount of palladium-carbon or rhodium-carbon in a solvent such as methanol, ethanol, tetrahydrofuran or acetonitrile at a temperature of from 0° C. to 50° C., preferably from 10° C. to 25° C.

Step K is a reaction for producing an α,β-unsaturated ketone by selective oxidation of the dihydroxycarboxylic acid ester, which can be conducted using activated manganese dioxide in a solvent such as ethyl ether, tetrahydrofuran, benzene or toluene at a temperature of from 20° C. to 80° C., preferably from 40° C. to 80° C.

Otherwise, the compound of the formula (I-6), can be synthesized from the an aldehyde of the formula (V) by the Wadsworth-Emmons coupling reaction (J. Amer. Chem. Soc., 107, 3731, (1985)).

Further, it can be synthesized from an enal of the formula (III) (Tetrahedron Letters, 26, 2951, (1985)). Further, the compound of the formula (I-7) can be obtained by adding a double anion of an acetoacetic acid ester in the same manner as in Step E to an aldehyde (VIII) synthesized from an aldehyde of the formula (V) by a continuous Wittig reaction (WO-8402131) to obtain a ketocarboxylic acid ester (IX) and further reducing the carbonyl group in the same manner as in Step F.

The compounds listed in Tables 1 to 4 including those disclosed in the subsequent Examples, are merely specific examples of the compound of the present invention. In the formulas, the substituent -Y-Z is shown in Table 1, and other substituents are shown in Tables 2 to 4.

In the following presentation of substituents, various symbols represent the following substituents.

Namely, n- represents normal, i- represents iso, sec-represents secondary, tert- represents tertiary, c-represents cyclo, Me represents methyl, Et represents ethyl, Pr represents propyl, Bu represents butyl, Pent represents pentyl, Hex represents hexyl, and Ph represents phenyl.

TABLE 1

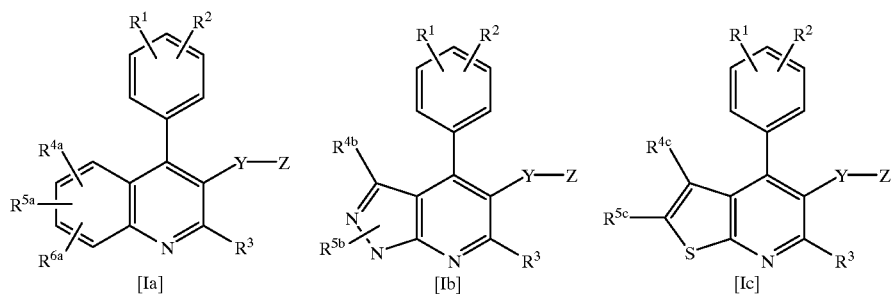

TABLE 1-continued
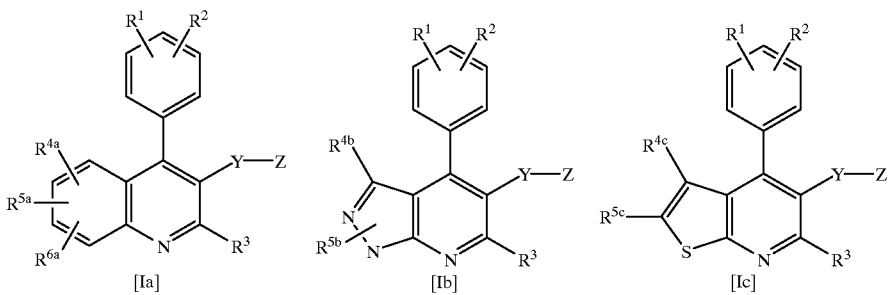
| Compound | | —Y—Z |
|---|---|---|
| I-2 | ($R^{12}$=H) | 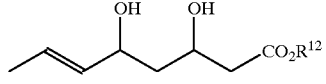 |
| I-3 | | 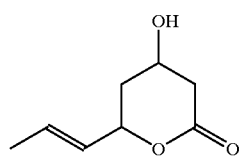 |
| I-4 | | 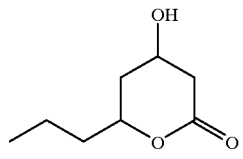 |
| I-5 | ($R^{12}$=Na) | 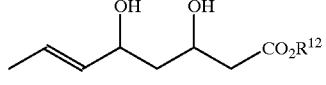 |
| I-6 | ($R^{12}$=Et) | 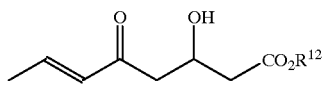 |
| I-7 | ($R^{12}$=Et) | 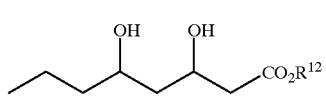 |
| I-8 | ($R^{12}$=H) | 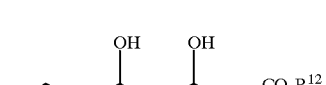 |
| I-9 | ($R^{12}$=Na) | 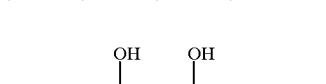 |
| II | ($R^{12}$=Et) | 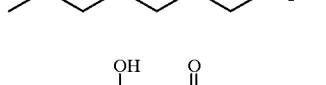 |
| IX | ($R^{12}$=Et) | 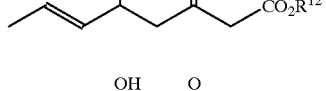 |

TABLE 2

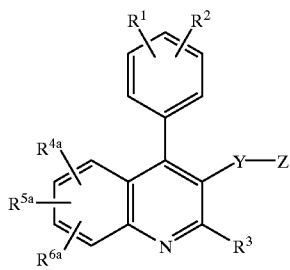

[Ia]

| $R^{4a}$ | $R^{5a}$ | $R^1$ | $R^2$ | $R^3$ | $R^{6a}$ |
|---|---|---|---|---|---|
| 6-OMe | H | H | H | i-Pr | H |
| 6-OMe | H | 4-F | H | i-Pr | H |
| 6-Br | H | 4-F | H | i-Pr | H |
| 6-Me | 8-Me | 4-F | H | i-Pr | H |
| 7-OMe | 8-OMe | 4-F | H | i-Pr | H |
| 6-Br | H | 2-F | H | i-Pr | H |
| 6,7-CH=CH—CH=CH— | | 4-F | H | i-Pr | H |
| H | H | 4-F | H | c-Hex | H |
| H | H | 4-Ph | H | i-Pr | H |
| H | H | 4-PhCH$_2$ | H | i-Pr | H |
| 6-Cl | H | 4-F | H | c-Pr | H |
| 6-Cl | H | 4-F | H | sec-Bu | H |
| 6-OCH$_2$Ph | H | 4-F | H | i-Pr | H |
| H | H | 4-F | H | i-Bu | H |
| H | H | 4-F | H | c-Pent | H |
| 6-Cl | H | 4-F | H | c-Pent | H |
| 6-Me$_2$N | H | 4-F | H | i-Pr | H |
| 6-Me | H | 4-F | H | c-Pr | H |
| 6-i-Pr | H | 4-F | H | i-Pr | H |
| 7-Me | H | 4-F | H | c-Pr | H |
| 6-OMe | H | 4-F | H | c-Pr | H |
| 6-Br | H | 4-F | H | c-Pr | H |
| 6-i-Pr | H | 4-F | H | c-Pr | H |
| 6-Cl | 8-Cl | 4-F | H | c-Pr | H |
| 5-F | 6-Br | 4-F | H | i-Pr | 8-Br |
| 6-OMe | 7-OMe | 4-F | H | i-Pr | 8-OMe |
| 6-Me | 7-Me | 4-F | H | i-Pr | 8-Me |
| 6-Cl | 7-Cl | 4-F | H | i-Pr | 8-Cl |
| H | H | 4-F | H | c-Bu | H |
| H | H | 4-F | H | c-Hex | H |
| 6-OMe | 7-OMe | H | H | i-Pr | H |
| 6-OMe | 7-OMe | 4-Cl | H | i-Pr | H |
| 6-OMe | 7-OMe | H | H | c-Pr | H |
| 6-OMe | 7-OMe | 4-Cl | H | c-Pr | H |
| 6-OMe | 7-OMe | 4-F | H | c-Pr | H |
| 6-Me | H | H | H | i-Pr | H |
| 6-Me | H | 4-Cl | H | i-Pr | H |
| 6-Me | H | H | H | c-Pr | H |
| 6-Me | H | 4-Cl | H | c-Pr | H |
| 6-Me | H | 4-F | H | c-Pr | H |
| 6-Cl | H | H | H | i-Pr | H |
| 6-Cl | H | 4-Cl | H | i-Pr | H |
| 6-Cl | H | H | H | c-Pr | H |
| 6-Cl | H | 4-Cl | H | c-Pr | H |
| 6-Cl | H | 4-F | H | c-Pr | H |
| H | H | H | H | i-Pr | H |
| H | H | 4-Cl | H | i-Pr | H |
| H | H | H | H | c-Pr | H |
| H | H | 4-Cl | H | c-Pr | H |
| H | H | 4-F | H | c-Pr | H |
| H | H | 4-Me | H | c-Pr | H |
| H | H | 4-n-Pent | H | c-Pr | H |
| H | H | 4-c-Pr | H | c-Pr | H |
| H | H | 4-c-Hex | H | c-Pr | H |
| H | H | 4-MeO | H | c-Pr | H |
| H | H | 4-n-BuO | H | c-Pr | H |
| H | H | 4-NMe | H | c-Pr | H |
| H | H | 4-NHEt | H | c-Pr | H |
| H | H | 4-CF$_3$ | H | c-Pr | H |
| H | H | 4-CF$_3$O | H | c-Pr | H |
| H | H | 4-Cl | H | c-Pr | H |
| H | H | 4-Br | H | c-Pr | H |

TABLE 2-continued

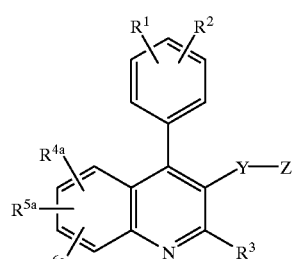

[Ia]

| $R^{4a}$ | $R^{5a}$ | $R^1$ | $R^2$ | $R^3$ | $R^{6a}$ |
|---|---|---|---|---|---|
| H | H | 4-PhO | H | c-Pr | H |
| H | H | 4-PhCH$_2$O | H | c-Pr | H |
| H | H | 4-OH | H | c-Pr | H |
| H | H | 4-OCH$_2$CH$_2$OH | H | c-Pr | H |
| H | H | 3,4-CH=CH—CH=CH— | H | c-Pr | H |
| H | H | 3,4-OCH$_2$O- | H | c-Pr | H |
| H | H | H | H | H | H |
| H | H | H | H | n-Pr | H |
| H | H | H | H | n-Pent | H |
| H | H | H | H | —CH=CH$_2$ | H |
| H | H | H | H | —CH=CHCH$_3$ | H |
| H | H | H | H | 3-c-Pentenyl | H |
| H | H | H | H | Ph | H |
| H | H | H | H | 4-Me—Ph | H |
| H | H | H | H | 4-MeO—Ph | H |
| H | H | H | H | 4-MeS—Ph | H |
| H | H | H | H | 4-Cl—Ph | H |
| H | H | H | H | 4-CF$_3$—Ph | H |
| H | H | H | H | 4-PhO—Ph | H |
| H | H | H | H | 4-OH—Ph | H |
| H | H | H | H | 4-CH$_2$OH—Ph | H |
| H | H | H | H | PhCH$_2$— | H |
| H | H | H | H | PhCH(Me) | H |
| 6-n-Pent | H | 4-F | H | c-Pr | H |
| 6-c-Pr | H | 4-F | H | c-Pr | H |
| 6-n-BuO | H | 4-F | H | c-Pr | H |
| 6-CF$_3$ | H | 4-F | H | c-Pr | H |
| 6-F | H | 4-F | H | c-Pr | H |
| 6-Ph | H | 4-F | H | c-Pr | H |
| 6-OH | H | 4-F | H | c-Pr | H |
| 6-HOCH$_2$ | H | 4-F | H | c-Pr | H |
| 6-MeOCH$_2$ | H | 4-F | H | c-Pr | H |
| 6,7-OCH$_2$O— | H | 4-F | H | c-Pr | H |

TABLE 3

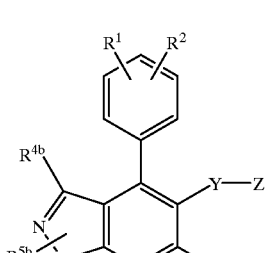

[Ib]

| $R^{4b}$ | $R^{5b}$ | $R^1$ | $R^2$ | $R^3$ |
|---|---|---|---|---|
| H | 2-Ph | 4-F | H | i-Pr |
| H | 1-Me | 4-F | H | i-Pr |
| H | 2-Me | 4-F | H | i-Pr |
| H | 1-i-Pr | 4-F | H | i-Pr |
| H | 1-tert-Bu | 4-F | H | i-Pr |
| H | 1-(4-Cl-Ph) | 4-F | H | i-Pr |
| H | 1-(4-Me-Ph) | 4-F | H | i-Pr |
| H | 1-(4-MeO-Ph) | 4-F | H | i-Pr |
| H | 1-(4-F-Ph) | 4-F | H | i-Pr |
| H | 1-CH$_2$Ph | 4-F | H | i-Pr |

TABLE 3-continued

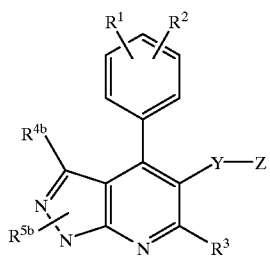

[Ib]

| R⁴ᵇ | R⁵ᵇ | R¹ | R² | R³ |
|---|---|---|---|---|
| Me | 2-Me | 4-F | H | i-Pr |
| Me | 1-Et | 4-F | H | i-Pr |
| Me | 1-i-Pr | 4-F | H | i-Pr |
| Me | 1-(4-Cl-Ph) | 4-F | H | i-Pr |
| Me | 1-(4-Me-Ph) | 4-F | H | i-Pr |
| Me | 1-(4-F-Ph) | 4-F | H | i-Pr |
| Me | 1-(2'-pyridyl) | 4-F | H | i-Pr |
| Et | 1-Me | 4-F | H | i-Pr |
| Et | 1-Et | 4-F | H | i-Pr |
| Et | 1-i-Pr | 4-F | H | i-Pr |
| Et | 1-Ph | 4-F | H | i-Pr |
| c-Pr | 1-Et | 4-F | H | i-Pr |
| c-Pr | 1-i-Pr | 4-F | H | i-Pr |
| c-Pr | 1-tert-Bu | 4-F | H | i-Pr |
| i-Pr | 1-Me | 4-F | H | i-Pr |
| i-Pr | 2-Me | 4-F | H | i-Pr |
| i-Pr | 1-Et | 4-F | H | i-Pr |
| i-Pr | 1-i-Pr | 4-F | H | i-Pr |
| i-Pr | 1-tert-Bu | 4-F | H | i-Pr |
| i-Pr | 2-Ph | 4-F | H | i-Pr |
| i-Pr | 1-Ph | 4-F | H | i-Pr |
| tert-Bu | 1-Me | 4-F | H | i-Pr |
| tert-Bu | 2-Me | 4-F | H | i-Pr |
| tert-Bu | 1-Et | 4-F | H | i-Pr |
| tert-Bu | 1-i-Pr | 4-F | H | i-Pr |
| tert-Bu | 1-tert-Bu | 4-F | H | i-Pr |
| tert-Bu | 1-Ph | 4-F | H | i-Pr |
| Ph | 1-Et | 4-F | H | i-Pr |
| Ph | 1-i-Pr | 4-F | H | i-Pr |
| Ph | 1-tert-Bu | 4-F | H | i-Pr |
| Ph | 1-Ph | 4-F | H | i-Pr |
| 4-Cl—Ph | 1-Et | 4-F | H | i-Pr |
| 4-Cl—Ph | 1-Ph | 4-F | H | i-Pr |
| 4-Me—Ph | 1-Me | 4-F | H | i-Pr |
| 4-MeO—Ph | 1-Me | 4-F | H | i-Pr |
| H | 1-Ph | 4-Cl | H | i-Pr |
| H | 1-Me | 4-Cl | H | i-Pr |
| H | 1-Et | 4-Cl | H | i-Pr |
| H | 1-i-Pr | 4-Cl | H | i-Pr |
| H | 1-tert-Bu | 4-Cl | H | i-Pr |
| H | 1-Ph | 4-Cl | H | i-Pr |
| H | 1-(4-Cl—Ph) | 4-Cl | H | i-Pr |
| H | 1-(4-Me—Ph) | 4-Cl | H | i-Pr |
| H | 1-(4-MeO—Ph) | 4-Cl | H | i-Pr |
| H | 1-(4-F—Ph) | 4-Cl | H | i-Pr |
| H | 1-CH₂Ph | 4-Cl | H | i-Pr |
| Me | 1-Me | 4-Cl | H | i-Pr |
| Me | 1-Et | 4-Cl | H | i-Pr |
| Me | 1-i-Pr | 4-Cl | H | i-Pr |
| Me | 1-(4-Cl—Ph) | 4-Cl | H | i-Pr |
| Me | 1-(4-Me—Ph) | 4-Cl | H | i-Pr |
| Me | 1-(4-MeO—Ph) | 4-Cl | H | i-Pr |
| Me | 1-(4-F—Ph) | 4-Cl | H | i-Pr |
| Me | 1-tert-Bu | 4-Cl | H | i-Pr |
| Me | 1-Ph | 4-Cl | H | i-Pr |
| Me | 1-CH₂Ph | 4-Cl | H | i-Pr |
| Me | 1-(2'-pyridyl) | 4-Cl | H | i-Pr |
| Et | 1-Me | 4-Cl | H | i-Pr |
| Et | 1-Et | 4-Cl | H | i-Pr |
| Et | 1-i-Pr | 4-Cl | H | i-Pr |
| Et | 1-Ph | 4-Cl | H | i-Pr |
| c-Pr | 1-Me | 4-Cl | H | i-Pr |

TABLE 3-continued

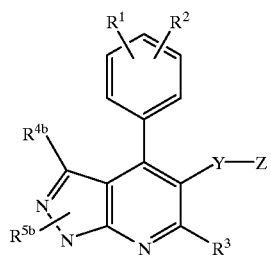

[Ib]

| R⁴ᵇ | R⁵ᵇ | R¹ | R² | R³ |
|---|---|---|---|---|
| c-Pr | 1-Et | 4-Cl | H | i-Pr |
| c-Pr | 1-i-Pr | 4-Cl | H | i-Pr |
| c-Pr | 1-tert-Bu | 4-Cl | H | i-Pr |
| i-Pr | 1-Me | 4-Cl | H | i-Pr |
| i-Pr | 1-Et | 4-Cl | H | i-Pr |
| i-Pr | 1-i-Pr | 4-Cl | H | i-Pr |
| i-Pr | 1-tert-Bu | 4-Cl | H | i-Pr |
| i-Pr | 1-Ph | 4-Cl | H | i-Pr |
| tert-Bu | 1-Me | 4-Cl | H | i-Pr |
| tert-Bu | 1-Et | 4-Cl | H | i-Pr |
| tert-Bu | 1-i-Pr | 4-Cl | H | i-Pr |
| tert-Bu | 1-tert-Bu | 4-Cl | H | i-Pr |
| tert-Bu | 1-Ph | 4-Cl | H | i-Pr |
| Ph | 1-Et | 4-Cl | H | i-Pr |
| Ph | 1-i-Pr | 4-Cl | H | i-Pr |
| Ph | 1-tert-Bu | 4-Cl | H | i-Pr |
| Ph | 1-Ph | 4-Cl | H | i-Pr |
| 4-Cl—Ph | 1-Me | 4-Cl | H | i-Pr |
| 4-Cl—Ph | 1-Et | 4-Cl | H | i-Pr |
| 4-Cl—Ph | 1-Ph | 4-Cl | H | i-Pr |
| 4-Me—Ph | 1-Me | 4-Cl | H | i-Pr |
| 4-MeO—Ph | 1-Me | 4-Cl | H | i-Pr |
| H | 1-Ph | H | H | i-Pr |
| H | 1-Me | H | H | i-Pr |
| H | 1-Et | H | H | i-Pr |
| H | 1-i-Pr | H | H | i-Pr |
| H | 1-tert-Bu | H | H | i-Pr |
| H | 1-(4-Cl—Ph) | H | H | i-Pr |
| H | 1-(4-Me—Ph) | H | H | i-Pr |
| H | 1-(4-MeO—Ph) | H | H | i-Pr |
| H | 1-(4-F—Ph) | H | H | i-Pr |
| H | 1-CH₂Ph | H | H | i-Pr |
| Me | 1-Me | H | H | i-Pr |
| Me | 1-Et | H | H | i-Pr |
| Me | 1-i-Pr | H | H | i-Pr |
| Me | 1-(4-Cl—Ph) | H | H | i-Pr |
| Me | 1-(4-Me—Ph) | H | H | i-Pr |
| Me | 1-(4-MeO—Ph) | H | H | i-Pr |
| Me | 1-(4-F—Ph) | H | H | i-Pr |
| Me | 1-tert-Bu | H | H | i-Pr |
| Me | 1-Ph | H | H | i-Pr |
| Me | 1-CH₂Ph | H | H | i-Pr |
| Me | 1-(2'-pyridyl) | H | H | i-Pr |
| Et | 1-Me | H | H | i-Pr |
| Et | 1-Et | H | H | i-Pr |
| Et | 1-i-Pr | H | H | i-Pr |
| Et | 1-Ph | H | H | i-Pr |
| c-Pr | 1-Me | H | H | i-Pr |
| c-Pr | 1-Et | H | H | i-Pr |
| c-Pr | 1-i-Pr | H | H | i-Pr |
| c-Pr | 1-tert-Bu | H | H | i-Pr |
| i-Pr | 1-Me | H | H | i-Pr |
| i-Pr | 1-Et | H | H | i-Pr |
| i-Pr | 1-i-Pr | H | H | i-Pr |
| i-Pr | 1-tert-Bu | H | H | i-Pr |
| i-Pr | 1-Ph | H | H | i-Pr |
| tert-Bu | 1-Me | H | H | i-Pr |
| tert-Bu | 1-Et | H | H | i-Pr |
| tert-Bu | 1-i-Pr | H | H | i-Pr |
| tert-Bu | 1-tert-Bu | H | H | i-Pr |
| tert-Bu | 1-Ph | H | H | i-Pr |
| Ph | 1-Et | H | H | i-Pr |

TABLE 3-continued

[Ib]

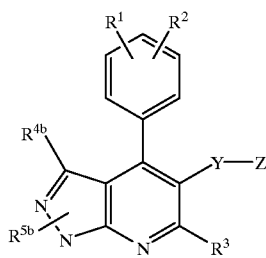

| $R^{4b}$ | $R^{5b}$ | $R^1$ | $R^2$ | $R^3$ |
|---|---|---|---|---|
| Ph | 1-i-Pr | H | H | i-Pr |
| Ph | 1-tert-Bu | H | H | i-Pr |
| Ph | 1-Ph | H | H | i-Pr |
| 4-Cl—Ph | 1-Me | H | H | i-Pr |
| 4-Cl—Ph | 1-Et | H | H | i-Pr |
| 4-Cl—Ph | 1-Ph | H | H | i-Pr |
| 4-Me—Ph | 1-Me | H | H | i-Pr |
| 4-MeO—Ph | 1-Me | H | H | i-Pr |
| H | 1-Ph | 4-F | H | c-Pr |
| H | 2-Ph | 4-F | H | c-Pr |
| H | 1-Me | 4-F | H | c-Pr |
| H | 2-Me | 4-F | H | c-Pr |
| H | 1-Et | 4-F | H | c-Pr |
| H | 1-i-Pr | 4-F | H | c-Pr |
| H | 1-tert-Bu | 4-F | H | c-Pr |
| H | 1-(4-Cl—Ph) | 4-F | H | c-Pr |
| H | 1-(4-Me—Ph) | 4-F | H | c-Pr |
| H | 1-(4-MeO—Ph) | 4-F | H | c-Pr |
| H | 1-(4-F—Ph) | 4-F | H | c-Pr |
| H | 1-CH$_2$Ph | 4-F | H | c-Pr |
| Me | 2-Me | 4-F | H | c-Pr |
| Me | 1-Et | 4-F | H | c-Pr |
| Me | 1-i-Pr | 4-F | H | c-Pr |
| Me | 1-(4-Cl—Ph) | 4-F | H | c-Pr |
| Me | 1-(4-Me—Ph) | 4-F | H | c-Pr |
| Me | 1-(4-MeO—Ph) | 4-F | H | c-Pr |
| Me | 1-(4-F—Ph) | 4-F | H | c-Pr |
| Me | 1-Ph | 4-F | H | c-Pr |
| Me | 2-Ph | 4-F | H | c-Pr |
| Me | 1-CH$_2$Ph | 4-F | H | c-Pr |
| Me | 1-(2'-pyridyl) | 4-F | H | c-Pr |
| Et | 1-Me | 4-F | H | c-Pr |
| Et | 1-Et | 4-F | H | c-Pr |
| Et | 1-i-Pr | 4-F | H | c-Pr |
| Et | 1-Ph | 4-F | H | c-Pr |
| c-Pr | 1-Me | 4-F | H | c-Pr |
| c-Pr | 1-Et | 4-F | H | c-Pr |
| c-Pr | 1-i-Pr | 4-F | H | c-Pr |
| c-Pr | 1-Ph | 4-F | H | c-Pr |
| i-Pr | 1-Me | 4-F | H | c-Pr |
| i-Pr | 2-Me | 4-F | H | c-Pr |
| i-Pr | 1-Et | 4-F | H | c-Pr |
| i-Pr | 1-i-Pr | 4-F | H | c-Pr |
| i-Pr | 1-tert-Bu | 4-F | H | c-Pr |
| i-Pr | 2-Ph | 4-F | H | c-Pr |
| i-Pr | 1-Ph | 4-F | H | c-Pr |
| tert-Bu | 1-Me | 4-F | H | c-Pr |
| tert-Bu | 2-Me | 4-F | H | c-Pr |
| tert-Bu | 1-Et | 4-F | H | c-Pr |
| tert-Bu | 1-i-Pr | 4-F | H | c-Pr |
| tert-Bu | 1-tert-Bu | 4-F | H | c-Pr |
| tert-Bu | 1-Ph | 4-F | H | c-Pr |
| Ph | 1-Et | 4-F | H | c-Pr |
| Ph | 1-i-Pr | 4-F | H | c-Pr |
| Ph | 1-Ph | 4-F | H | c-Pr |
| 4-Cl—Ph | 1-Me | 4-F | H | c-Pr |
| 4-Cl—Ph | 1-Et | 4-F | H | c-Pr |
| 4-Cl—Ph | 1-Ph | 4-F | H | c-Pr |
| 4-Me—Ph | 1-Me | 4-F | H | c-Pr |
| 4-MeO—Ph | 1-Me | 4-F | H | c-Pr |
| H | 1-Ph | 4-Cl | H | c-Pr |
| H | 1-Me | 4-Cl | H | c-Pr |

TABLE 3-continued

[Ib]

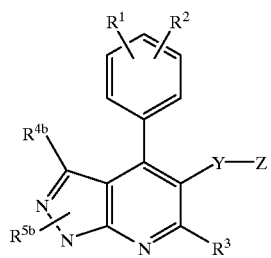

| $R^{4b}$ | $R^{5b}$ | $R^1$ | $R^2$ | $R^3$ |
|---|---|---|---|---|
| H | 1-Et | 4-Cl | H | c-Pr |
| H | 1-i-Pr | 4-Cl | H | c-Pr |
| H | 1-tert-Bu | 4-Cl | H | c-Pr |
| H | 1-Ph | 4-Cl | H | c-Pr |
| H | 1-(4-Cl—Ph) | 4-Cl | H | c-Pr |
| H | 1-(4-Me—Ph) | 4-Cl | H | c-Pr |
| H | 1-(4-MeO—Ph) | 4-Cl | H | c-Pr |
| H | 1-(4-F—Ph) | 4-Cl | H | c-Pr |
| H | 1-CH$_2$Ph | 4-Cl | H | c-Pr |
| Me | 1-Me | 4-Cl | H | c-Pr |
| Me | 1-Et | 4-Cl | H | C-Pr |
| Me | 1-i-Pr | 4-Cl | H | c-Pr |
| Me | 1-(4-Cl—Ph) | 4-Cl | H | c-Pr |
| Me | 1-(4-Me—Ph) | 4-Cl | H | c-Pr |
| Me | 1-(4-MeO—Ph) | 4-Cl | H | c-Pr |
| Me | 1-(4-F—Ph) | 4-Cl | H | c-Pr |
| Me | 1-tert-Bu | 4-Cl | H | c-Pr |
| Me | 1-Ph | 4-Cl | H | c-Pr |
| Me | 1-CH$_2$Ph | 4-Cl | H | c-Pr |
| Me | 1-(2'-pyridyl) | 4-Cl | H | c-Pr |
| Et | 1-Me | 4-Cl | H | c-Pr |
| Et | 1-Et | 4-Cl | H | c-Pr |
| Et | 1-i-Pr | 4-Cl | H | c-Pr |
| Et | 1-Ph | 4-Cl | H | c-Pr |
| c-Pr | 1-Me | 4-Cl | H | c-Pr |
| c-Pr | 1-Et | 4-Cl | H | c-Pr |
| c-Pr | 1-i-Pr | 4-Cl | H | c-Pr |
| c-Pr | 1-tert-Bu | 4-Cl | H | c-Pr |
| i-Pr | 1-Me | 4-Cl | H | c-Pr |
| i-Pr | 1-Et | 4-Cl | H | c-Pr |
| i-Pr | 1-i-Pr | 4-Cl | H | c-Pr |
| i-Pr | 1-tert-Bu | 4-Cl | H | c-Pr |
| i-Pr | 1-Ph | 4-Cl | H | c-Pr |
| tert-Bu | 1-Me | 4-Cl | H | c-Pr |
| tert-Bu | 1-Et | 4-Cl | H | c-Pr |
| tert-Bu | 1-i-Pr | 4-Cl | H | c-Pr |
| tert-Bu | 1-tert-Bu | 4-Cl | H | c-Pr |
| tert-Bu | 1-Ph | 4-Cl | H | c-Pr |
| Ph | 1-Et | 4-Cl | H | c-Pr |
| Ph | 1-i-Pr | 4-Cl | H | c-Pr |
| Ph | 1-tert-Bu | 4-Cl | H | c-Pr |
| Ph | 1-Ph | 4-Cl | H | c-Pr |
| 4-Cl—Ph | 1-Me | 4-Cl | H | c-Pr |
| 4-Cl—Ph | 1-Et | 4-Cl | H | c-Pr |
| 4-Cl—Ph | 1-Ph | 4-Cl | H | c-Pr |
| 4-Me—Ph | 1-Me | 4-Cl | H | c-Pr |
| 4-MeO—Ph | 1-Me | 4-Cl | H | c-Pr |
| H | 1-Ph | H | H | c-Pr |
| H | 1-Me | H | H | c-Pr |
| H | 1-Et | H | H | c-Pr |
| H | 1-i-Pr | H | H | c-Pr |
| H | 1-tert-Bu | H | H | c-Pr |
| H | 1-(4-Cl—Ph) | H | H | c-Pr |
| H | 1-(4-Me—Ph) | H | H | c-Pr |
| H | 1-(4-MeO—Ph) | H | H | c-Pr |
| H | 1-(4-F—Ph) | H | H | c-Pr |
| H | 1-CH$_2$Ph | H | H | c-Pr |
| Me | 1-Me | H | H | c-Pr |
| Me | 1-Et | H | H | c-Pr |
| Me | 1-i-Pr | H | H | c-Pr |
| Me | 1-(4-Cl—Ph) | H | H | c-Pr |
| Me | 1-(4-Me—Ph) | H | H | c-Pr |

TABLE 3-continued

[Ib]

| $R^{4b}$ | $R^{5b}$ | $R^1$ | $R^2$ | $R^3$ |
|---|---|---|---|---|
| Me | 1-(4-MeO—Ph) | H | H | c-Pr |
| Me | 1-(4-F—Ph) | H | H | c-Pr |
| Me | 1-tert-Bu | H | H | c-Pr |
| Me | 1-Ph | H | H | c-Pr |
| Me | 1-CH$_2$Ph | H | H | c-Pr |
| Me | 1-(2'-pyridyl) | H | H | c-Pr |
| Et | 1-Me | H | H | c-Pr |
| Et | 1-Et | H | H | c-Pr |
| Et | 1-i-Pr | H | H | c-Pr |
| Et | 1-Ph | H | H | c-Pr |
| c-Pr | 1-Me | H | H | c-Pr |
| c-Pr | 1-Et | H | H | c-Pr |
| c-Pr | 1-i-Pr | H | H | c-Pr |
| c-Pr | 1-tert-Bu | H | H | c-Pr |
| i-Pr | 1-Me | H | H | c-Pr |
| i-Pr | 1-Et | H | H | c-Pr |
| i-Pr | 1-i-Pr | H | H | c-Pr |
| i-Pr | 1-tert-Bu | H | H | c-Pr |
| i-Pr | 1-Ph | H | H | c-Pr |
| tert-Bu | 1-Me | H | H | c-Pr |
| tert-Bu | 1-Et | H | H | c-Pr |
| tert-Bu | 1-i-Pr | H | H | c-Pr |
| tert-Bu | 1-tert-Bu | H | H | c-Pr |
| tert-Bu | 1-Ph | H | H | c-Pr |
| Ph | 1-Et | H | H | c-Pr |
| Ph | 1-i-Pr | H | H | c-Pr |
| Ph | 1-tert-Bu | H | H | c-Pr |
| Ph | 1-Ph | H | H | c-Pr |
| 4-Cl—Ph | 1-Me | H | H | c-Pr |
| 4-Cl—Ph | 1-Et | H | H | c-Pr |
| 4-Cl—Ph | 1-Ph | H | H | c-Pr |
| 4-Me—Ph | 1-Me | H | H | c-Pr |
| 4-MeO—Ph | 1-Me | H | H | c-Pr |
| n-Oct | 1-Me | 4-F | H | c-Pr |
| MeO | 1-Me | 4-F | H | c-Pr |
| n-BuO | 1-Me | 4-F | H | c-Pr |
| c-Hex | 1-Me | 4-F | H | c-Pr |
| —CH=CH$_2$ | 1-Me | 4-F | H | c-Pr |
| —CH=CHCH$_3$ | 1-Me | 4-F | H | c-Pr |
| α-naphthyl | 1-Me | 4-F | H | c-Pr |
| β-naphthyl | 1-Me | 4-F | H | c-Pr |
| 3-pyridyl | 1-Me | 4-F | H | c-Pr |
| 2-thienyl | 1-Me | 4-F | H | c-Pr |
| 2-furyl | 1-Me | 4-F | H | c-Pr |
| F | 1-Me | 4-F | H | c-Pr |
| Cl | 1-Me | 4-F | H | c-Pr |
| Br | 1-Me | 4-F | H | c-Pr |
| 4-n-Hex-Ph | 1-Me | 4-F | H | c-Pr |
| 4-n-BuO—Ph | 1-Me | 4-F | H | c-Pr |
| 4-MeS—Ph | 1-Me | 4-F | H | c-Pr |
| 4-Me$_2$N—Ph | 1-Me | 4-F | H | c-Pr |
| 4-ClCH$_2$—Ph | 1-Me | 4-F | H | c-Pr |
| 4-CF$_3$—Ph | 1-Me | 4-F | H | c-Pr |
| 4-PhO—Ph | 1-Me | 4-F | H | c-Pr |
| 4-OH—Ph | 1-Me | 4-F | H | c-Pr |
| 4-HOCH$_2$—Ph | 1-Me | 4-F | H | c-Pr |
| 3,4-OCH$_2$O—Ph | 1-Me | 4-F | H | c-Pr |
| 4-Ph—Ph | 1-Me | 4-F | H | c-Pr |
| Ph—CH=CH— | 1-Me | 4-F | H | c-Pr |
| PhCH$_2$— | 1-Me | 4-F | H | c-Pr |
| 4-Me—PhCH$_2$— | 1-Me | 4-F | H | c-Pr |
| 4-Cl—PhCH$_2$ | 1-Me | 4-F | H | c-Pr |
| PhCH(Me)— | 1-Me | 4-F | H | c-Pr |
| MeOCH$_2$— | 1-Me | 4-F | H | c-Pr |
| MeOCH$_2$CH$_2$— | 1-Me | 4-F | H | c-Pr |
| Me | 1-H | 4-F | H | c-Pr |
| Me | 1-n-Hex | 4-F | H | c-Pr |
| Me | 1-CF$_3$ | 4-F | H | c-Pr |
| Me | 1-c-Pr | 4-F | H | c-Pr |
| Me | 1-c-Hex | 4-F | H | c-Pr |
| Me | 1-α-naphthyl | 4-F | H | c-Pr |
| Me | 1-β-naphthyl | 4-F | H | c-Pr |
| Me | 1-(3'-pyridyl) | 4-F | H | c-Pr |
| Me | 1-(2'-pyridyl) | 4-F | H | c-Pr |
| Me | 1-(2'-thienyl) | 4-F | H | c-Pr |
| Me | 1-(2'-furyl) | 4-F | H | c-Pr |
| Me | 1-(4-MeS—Ph) | 4-F | H | c-Pr |
| Me | 1-(4-Me$_2$N—Ph) | 4-F | H | c-Pr |
| Me | 1-(4-ClCH$_2$—Ph) | 4-F | H | c-Pr |
| Me | 1-(4-CF$_3$—Ph) | 4-F | H | c-Pr |
| Me | 1-(4-PhO—Ph) | 4-F | H | c-Pr |
| Me | 1-(4-OH—Ph) | 4-F | H | c-Pr |
| Me | 1-(4-HOCH$_2$—Ph) | 4-F | H | c-Pr |
| Me | 1-(3,4-OCH$_2$O—Ph) | 4-F | H | c-Pr |
| Me | 1-(4-Ph—Ph) | 4-F | H | c-Pr |
| Me | 1-(4-Me—PHCH$_2$) | 4-F | H | c-Pr |
| Me | 1-(4-Cl—PhCH$_2$) | 4-F | H | c-Pr |
| Me | 1-PhCH(Me) | 4-F | H | c-Pr |
| Me | 1-MeOCH$_2$— | 4-F | H | c-Pr |
| Me | 1-MeOCH$_2$CH$_2$— | 4-F | H | c-Pr |

TABLE 4

[Ic]

| $R^{4c}$ | $R^{5c}$ | $R^1$ | $R^2$ | $R^3$ |
|---|---|---|---|---|
| H | H | H | H | i-Pr |
| H | H | 4-F | H | i-Pr |
| H | H | 4-Cl | H | i-Pr |
| H | H | 3-Me | 4-F | i-Pr |
| H | H | H | H | c-Pr |
| H | H | 4-F | H | c-Pr |
| H | H | 4-Cl | H | c-Pr |
| H | H | 3-Me | 4-F | c-Pr |
| Me | H | H | H | i-Pr |
| Me | H | 4-F | H | i-Pr |
| Me | H | 4-Cl | H | i-Pr |
| Me | H | 3-Me | 4-F | i-Pr |
| Me | H | H | H | c-Pr |

TABLE 4-continued

[Ic]

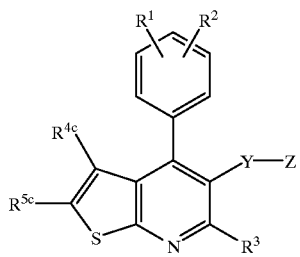

| R4c | R5c | R1 | R2 | R3 |
|---|---|---|---|---|
| Me | H | 4-F | H | c-Pr |
| Me | H | 4-Cl | H | c-Pr |
| Me | H | 3-Me | 4-F | c-Pr |
| Et | H | H | H | i-Pr |
| Et | H | 4-F | H | i-Pr |
| Et | H | 4-Cl | H | i-Pr |
| Et | H | 3-Me | 4-F | i-Pr |
| Et | H | H | H | c-Pr |
| Et | H | 4-F | H | c-Pr |
| Et | H | 4-Cl | H | c-Pr |
| Et | H | 3-Me | 4-F | c-Pr |
| Et | Me | H | H | i-Pr |
| Et | Me | 4-F | H | i-Pr |
| Et | Me | 4-Cl | H | i-Pr |
| Et | Me | 3-Me | 4-F | i-Pr |
| Et | Me | H | H | c-Pr |
| Et | Me | 4-F | H | c-Pr |
| Et | Me | 4-Cl | H | c-Pr |
| Et | Me | 3-Me | 4-F | c-Pr |
| n-Pr | H | H | H | i-Pr |
| n-Pr | H | 4-F | H | i-Pr |
| n-Pr | H | 4-Cl | H | i-Pr |
| n-Pr | H | 3-Me | 4-F | i-Pr |
| n-Pr | H | H | H | c-Pr |
| n-Pr | H | 4-F | H | c-Pr |
| n-Pr | H | 4-Cl | H | c-Pr |
| n-Pr | H | 3-Me | 4-F | c-Pr |
| i-Pr | H | H | H | i-Pr |
| i-Pr | H | 4-F | H | i-Pr |
| i-Pr | H | 4-Cl | H | i-Pr |
| i-Pr | H | 3-Me | 4-F | i-Pr |
| i-Pr | H | H | H | c-Pr |
| i-Pr | H | 4-F | H | c-Pr |
| i-Pr | H | 4-Cl | H | c-Pr |
| i-Pr | H | 3-Me | 4-F | c-Pr |
| n-Bu | H | H | H | i-Pr |
| n-Bu | H | 4-F | H | i-Pr |
| n-Bu | H | 4-Cl | H | i-Pr |
| n-Bu | H | 3-Me | 4-F | i-Pr |
| n-Bu | H | H | H | c-Pr |
| n-Bu | H | 4-F | H | c-Pr |
| n-Bu | H | 4-Cl | H | c-Pr |
| n-Bu | H | 3-Me | 4-F | c-Pr |
| i-Bu | H | H | H | i-Pr |
| i-Bu | H | 4-F | H | i-Pr |
| i-Bu | H | 4-Cl | H | i-Pr |
| i-Bu | H | 3-Me | 4-F | i-Pr |
| i-Bu | H | H | H | c-Pr |
| i-Bu | H | 4-F | H | c-Pr |
| i-Bu | H | 4-Cl | H | c-Pr |
| i-Bu | H | 3-Me | 4-F | c-Pr |
| c-Pent-Me | H | H | H | i-Pr |
| c-Pent-Me | H | 4-F | H | i-Pr |
| c-Pent-Me | H | 4-Cl | H | i-Pr |
| c-Pent-Me | H | 3-Me | 4-F | i-Pr |
| c-Pent-Me | H | H | H | c-Pr |
| c-Pent-Me | H | 4-F | H | c-Pr |
| c-Pent-Me | H | 4-Cl | H | c-Pr |
| c-Pent-Me | H | 3-Me | 4-F | c-Pr |
| c-Pr | H | H | H | i-Pr |
| c-Pr | H | 4-F | H | i-Pr |
| c-Pr | H | 4-Cl | H | i-Pr |
| c-Pr | H | 3-Me | 4-F | i-Pr |
| c-Pr | H | H | H | c-Pr |
| c-Pr | H | 4-F | H | c-Pr |
| c-Pr | H | 4-Cl | H | c-Pr |
| c-Pr | H | 3-Me | 4-F | c-Pr |
| H | Ph | H | H | i-Pr |
| H | Ph | 4-F | H | i-Pr |
| H | Ph | 4-Cl | H | i-Pr |
| H | Ph | 3-Me | 4-F | i-Pr |
| H | Ph | H | H | c-Pr |
| H | Ph | 4-F | H | c-Pr |
| H | Ph | 4-Cl | H | c-Pr |
| H | Ph | 3-Me | 4-F | c-Pr |
| Ph | Me | H | H | i-Pr |
| Ph | Me | 4-F | H | i-Pr |
| Ph | Me | 4-Cl | H | i-Pr |
| Ph | Me | 3-Me | 4-F | i-Pr |
| Ph | Me | H | H | c-Pr |
| Ph | Me | 4-F | H | c-Pr |
| Ph | Me | 4-Cl | H | c-Pr |
| Ph | Me | 3-Me | 4-F | c-Pr |
| H | Me | H | H | i-Pr |
| H | Me | 4-F | H | i-Pr |
| H | Me | 4-Cl | H | i-Pr |
| H | Me | 3-Me | 4-F | i-Pr |
| H | Me | H | H | c-Pr |
| H | Me | 4-F | H | c-Pr |
| H | Me | 4-Cl | H | c-Pr |
| H | Me | 3-Me | 4-F | c-Pr |
| H | i-Pr | H | H | i-Pr |
| H | i-Pr | 4-F | H | i-Pr |
| H | i-Pr | 4-Cl | H | i-Pr |
| H | i-Pr | 3-Me | 4-F | i-Pr |
| H | i-Pr | H | H | c-Pr |
| H | i-Pr | 4-F | H | c-Pr |
| H | i-Pr | 4-Cl | H | c-Pr |
| H | i-Pr | 3-Me | 4-F | c-Pr |
| H | Et | H | H | i-Pr |
| H | Et | 4-F | H | i-Pr |
| H | Et | 4-Cl | H | i-Pr |
| H | Et | 3-Me | 4-F | i-Pr |
| H | Et | H | H | c-Pr |
| H | Et | 4-F | H | c-Pr |
| H | Et | 4-Cl | H | c-Pr |
| H | Et | 3-Me | 4-F | c-Pr |
| H | n-Pr | H | H | i-Pr |
| H | n-Pr | 4-F | H | i-Pr |
| H | n-Pr | 4-Cl | H | i-Pr |
| H | n-Pr | 3-Me | 4-F | i-Pr |
| H | n-Pr | H | H | c-Pr |
| H | n-Pr | 4-F | H | c-Pr |
| H | n-Pr | 4-Cl | H | c-Pr |
| H | n-Pr | 3-Me | 4-F | c-Pr |
| H | n-Bu | H | H | i-Pr |
| H | n-Bu | 4-F | H | i-Pr |
| H | n-Bu | 4-Cl | H | i-Pr |
| H | n-Bu | 3-Me | 4-F | i-Pr |
| H | n-Bu | H | H | c-Pr |
| H | n-Bu | 4-F | H | c-Pr |
| H | n-Bu | 4-Cl | H | c-Pr |
| H | n-Bu | 3-Me | 4-F | c-Pr |
| Me | Me | H | H | i-Pr |

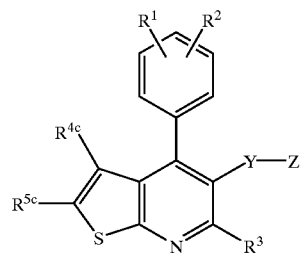

TABLE 4-continued

[Ic]

| $R^{4c}$ | $R^{5c}$ | $R^1$ | $R^2$ | $R^3$ |
|---|---|---|---|---|
| Me | Me | 4-F | H | i-Pr |
| Me | Me | 4-Cl | H | i-Pr |
| Me | Me | 3-Me | 4-F | i-Pr |
| Me | Me | H | H | c-Pr |
| Me | Me | 4-F | H | c-Pr |
| Me | Me | 4-Cl | H | c-Pr |
| Me | Me | 3-Me | 4-F | c-Pr |
| c-Pent-Me | Me | H | H | i-Pr |
| c-Pent-Me | Me | 4-F | H | i-Pr |
| c-Pent-Me | Me | 4-Cl | H | i-Pr |
| c-Pent-Me | Me | 3-Me | 4-F | i-Pr |
| c-Pent-Me | Me | H | H | c-Pr |
| c-Pent-Me | Me | 4-F | H | c-Pr |
| c-Pent-Me | Me | 4-Cl | H | c-Pr |
| c-Pent-Me | Me | 3-Me | 4-F | c-Pr |
| n-Pr | Et | H | H | i-Pr |
| n-Pr | Et | 4-F | H | i-Pr |
| n-Pr | Et | 4-Cl | H | i-Pr |
| n-Pr | Et | 3-Me | 4-F | i-Pr |
| n-Pr | Et | H | H | c-Pr |
| n-Pr | Et | 4-F | H | c-Pr |
| n-Pr | Et | 4-Cl | H | c-Pr |
| n-Pr | Et | 3-Me | 4-F | c-Pr |
| n-Bu | n-Pr | H | H | i-Pr |
| n-Bu | n-Pr | 4-F | H | i-Pr |
| n-Bu | n-Pr | 4-Cl | H | i-Pr |
| n-Bu | n-Pr | 3-Me | 4-F | i-Pr |
| n-Bu | n-Pr | H | H | c-Pr |
| n-Bu | n-Pr | 4-F | H | c-Pr |
| n-Bu | n-Pr | 4-Cl | H | c-Pr |
| n-Bu | n-Pr | 3-Me | 4-F | c-Pr |
| Cl | Me | H | H | i-Pr |
| Cl | Me | 4-F | H | i-Pr |
| Cl | Me | 4-Cl | H | i-Pr |
| Cl | Me | 3-Me | 4-F | i-Pr |
| Cl | Me | H | H | c-Pr |
| Cl | Me | 4-F | H | c-Pr |
| Cl | Me | 4-Cl | H | c-Pr |
| Cl | Me | 3-Me | 4-F | c-Pr |
| Cl | i-Pr | H | H | i-Pr |
| Cl | i-Pr | 4-F | H | i-Pr |
| Cl | i-Pr | 4-Cl | H | i-Pr |
| Cl | i-Pr | 3-Me | 4-F | i-Pr |
| Cl | i-Pr | H | H | c-Pr |
| Cl | i-Pr | 4-F | H | c-Pr |
| Cl | i-Pr | 4-Cl | H | c-Pr |
| Cl | i-Pr | 3-Me | 4-F | c-Pr |
| MeO | Me | H | H | i-Pr |
| MeO | Me | 4-F | H | i-Pr |
| MeO | Me | 4-Cl | H | i-Pr |
| MeO | Me | 3-Me | 4-F | i-Pr |
| MeO | Me | H | H | c-Pr |
| MeO | Me | 4-F | H | c-Pr |
| MeO | Me | 4-Cl | H | c-Pr |
| MeO | Me | 3-Me | 4-F | c-Pr |
| MeO | i-Pr | H | H | i-Pr |
| MeO | i-Pr | 4-F | H | i-Pr |
| MeO | i-Pr | 4-Cl | H | i-Pr |
| MeO | i-Pr | 3-Me | 4-F | i-Pr |
| MeO | i-Pr | H | H | c-Pr |
| MeO | i-Pr | 4-F | H | c-Pr |
| MeO | i-Pr | 4-Cl | H | c-Pr |
| MeO | i-Pr | 3-Me | 4-F | c-Pr |
| $Me_2N$ | Me | H | H | i-Pr |
| $Me_2N$ | Me | 4-F | H | i-Pr |
| $Me_2N$ | Me | 4-Cl | H | i-Pr |
| $Me_2N$ | Me | 3-Me | 4-F | i-Pr |
| $Me_2N$ | Me | H | H | c-Pr |
| $Me_2N$ | Me | 4-F | H | c-Pr |
| $Me_2N$ | Me | 4-Cl | H | c-Pr |
| $Me_2N$ | Me | 3-Me | 4-F | c-Pr |
| Cl | Cl | H | H | i-Pr |
| Cl | Cl | 4-F | H | i-Pr |
| Cl | Cl | 4-Cl | H | i-Pr |
| Cl | Cl | 3-Me | 4-F | i-Pr |
| Cl | Cl | H | H | c-Pr |
| Cl | Cl | 4-F | H | c-Pr |
| Cl | Cl | 4-Cl | H | c-Pr |
| Cl | Cl | 3-Me | 4-F | c-Pr |
| H | Br | H | H | i-Pr |
| H | Br | 4-F | H | i-Pr |
| H | Br | 4-Cl | H | i-Pr |
| H | Br | 3-Me | 4-F | i-Pr |
| H | Br | H | H | c-Pr |
| H | Br | 4-F | H | c-Pr |
| H | Br | 4-Cl | H | c-Pr |
| H | Br | 3-Me | 4-F | c-Pr |
| H | Hex | H | H | i-Pr |
| H | Hex | 4-F | H | i-Pr |
| H | Hex | 4-Cl | H | i-Pr |
| H | Hex | 3-Me | 4-F | i-Pr |
| H | Hex | H | H | c-Pr |
| H | Hex | 4-F | H | c-Pr |
| H | Hex | 4-Cl | H | c-Pr |
| H | Hex | 3-Me | 4-F | c-Pr |
| H | —CH=$CH_2$ | H | H | i-Pr |
| H | —CH=$CH_2$ | 4-F | H | i-Pr |
| H | —CH=$CH_2$ | 4-Cl | H | i-Pr |
| H | —CH=$CH_2$ | 3-Me | 4-F | i-Pr |
| H | —CH=$CH_2$ | H | H | c-Pr |
| H | —CH=$CH_2$ | 4-F | H | c-Pr |
| H | —CH=$CH_2$ | 4-Cl | H | c-Pr |
| H | —CH=$CH_2$ | 3-Me | 4-F | c-Pr |
| $PhCH_2$ | Ph | H | H | i-Pr |
| $PhCH_2$ | Ph | 4-F | H | i-Pr |
| $PhCH_2$ | Ph | 4-Cl | H | i-Pr |
| $PhCH_2$ | Ph | 3-Me | 4-F | i-Pr |
| $PhCH_2$ | Ph | H | H | c-Pr |
| $PhCH_2$ | Ph | 4-F | H | c-Pr |
| $PhCH_2$ | Ph | 4-Cl | H | c-Pr |
| $PhCH_2$ | Ph | 3-Me | 4-F | c-Pr |
| 2-naphthyl | Me | H | H | i-Pr |
| 2-naphthyl | Me | 4-F | H | i-Pr |
| 2-naphthyl | Me | 4-Cl | H | i-Pr |
| 2-naphthyl | Me | 3-Me | 4-F | i-Pr |
| 2-naphthyl | Me | H | H | c-Pr |
| 2-naphthyl | Me | 4-F | H | c-Pr |
| 2-naphthyl | Me | 4-Cl | H | c-Pr |
| 2-naphthyl | Me | 3-Me | 4-F | c-Pr |
| 3-Pyridyl | Me | H | H | i-Pr |
| 3-Pyridyl | Me | 4-F | H | i-Pr |
| 3-Pyridyl | Me | 4-Cl | H | i-Pr |
| 3-Pyridyl | Me | 3-Me | 4-F | i-Pr |
| 3-Pyridyl | Me | H | H | c-Pr |

TABLE 4-continued

[Ic]

structure: R¹, R² on phenyl ring attached to position 4 of thieno[2,3-b]pyridine core with R⁴ᶜ at position 3, R⁵ᶜ at position 2, Y—Z at position 5, R³ at position 6

| R⁴ᶜ | R⁵ᶜ | R¹ | R² | R³ |
|---|---|---|---|---|
| 3-Pyridyl | Me | 4-F | H | c-Pr |
| 3-Pyridyl | Me | 4-Cl | H | c-Pr |
| 3-Pyridyl | Me | 3-Me | 4-F | c-Pr |
| H | H | H | H | H |
| H | H | 4-F | H | H |
| H | H | 4-Cl | H | H |
| H | H | 3-Me | 4-F | H |
| H | H | H | H | Me |
| H | H | 4-F | H | Me |
| H | H | 4-Cl | H | Me |
| H | H | 3-Me | 4-F | Me |
| H | H | H | H | Et |
| H | H | 4-F | H | Et |
| H | H | 4-Cl | H | Et |
| H | H | 3-Me | 4-F | Et |
| H | H | H | H | n-Pr |
| H | H | 4-F | H | n-Pr |
| H | H | 4-Cl | H | n-Pr |
| H | H | 3-Me | 4-F | n-Pr |
| H | H | H | H | n-Hex |
| H | H | 4-F | H | n-Hex |
| H | H | 4-Cl | H | n-Hex |
| H | H | 3-Me | 4-F | n-Hex |
| H | H | H | H | —C(CH₃)=CH₂ |
| H | H | 4-F | H | —C(CH₃)=CH₂ |
| H | H | 4-Cl | H | —C(CH₃)=CH₂ |
| H | H | 3-Me | 4-F | —C(CH₃)=CH₂ |
| H | H | H | H | c-Hex |
| H | H | 4-F | H | c-Hex |
| —CH=CH—CH₃ | Me | 4-F | H | c-Pr |
| c-Hex | Me | 4-F | H | c-Pr |
| n-BuO | Me | 4-F | H | c-Pr |
| 4-MeO—Ph | Me | 4-F | H | c-Pr |
| 4-Cl—Ph | Me | 4-F | H | c-Pr |
| 4-Me—Ph | Me | 4-F | H | c-Pr |
| 3-CF₃—Ph | Me | 4-F | H | c-Pr |
| 2-pyrimidyl | Me | 4-F | H | c-Pr |
| 2-thienyl | Me | 4-F | H | c-Pr |
| 2-furyl | Me | 4-F | H | c-Pr |
| PhO | Me | 4-F | H | c-Pr |
| 4-MeO—PhO | Me | 4-F | H | c-Pr |
| 4-Cl—PhO | Me | 4-F | H | c-Pr |
| 4-MeO—PhO | Me | 4-F | H | c-Pr |
| 3-CF₃—PhO | Me | 4-F | H | c-Pr |
| —NHCH₂Ph | Me | 4-F | H | c-Pr |
| piperazyl | Me | 4-F | H | c-Pr |
| 4-Me—PhCH₂ | Me | 4-F | H | c-Pr |
| 4-MeO—PhCH₂ | Me | 4-F | H | c-Pr |
| 4-Cl—PhCH₂ | Me | 4-F | H | c-Pr |
| 3-CF₃—PhCH₂ | Me | 4-F | H | c-Pr |
| PhCH₂CH₂ | Me | 4-F | H | c-Pr |
| —(CH₂)₂—CH(Ph)CH₂— | | 4-F | H | c-Pr |
| —(CH₂)₂—CH(c-Pr)CH₂— | | 4-F | H | c-Pr |
| —CH₂—CH=CH—CH₂— | | 4-F | H | c-Pr |
| —(CH₂)₂N(CH₂Ph)CH₂— | | 4-F | H | c-Pr |

Further, in a similar manner, it is possible to prepare pharmacologically acceptable salts such as potassium salts or ½ calcium salts, esters such as methyl esters, n-propyl esters, i-propyl esters, c-propyl esters, n-butyl esters, i-butyl esters, sec-butyl esters, tert-butyl esters, n-pentyl esters, i-pentyl esters or n-hexyl esters, and ammonium salts, trimethylamine salts, diethylamine salts, piperazine salts, morpholine salts, piperidine salts, auramine salts, diauramine salts or tromethamine salts, of these compounds.

The compounds of the present invention not only have high inhibitory activities against biosynthesis of cholesterol wherein HMG-CoA reductase acts as the rate limiting enzyme, but also have inhibitory effects against migration of M-SMC, proliferation of I-SMC and cell adhesion of blood cells to endothelial cells, as shown by the test results given hereinafter. Thus, the compounds of the present invention are useful as curing agents against hyperlipidemia, hyperlipoproteinemia and atherosclerosis.

They may be formulated into various suitable formulations depending upon the manner of the administration. The compounds of the present invention may be administered in the form of free acids or in the form of physiologically hydrolyzable and acceptable esters or lactones, or pharmaceutically acceptable salts.

The pharmaceutical composition of the present invention is preferably administered orally in the form of the compound of the present invention by itself or in the form of powders, granules, tablets or capsules formulated by mixing the compound of the present invention with a suitable pharmaceutically acceptable carrier including a binder such as hydroxypropyl cellulose, syrup, gum arabic, gelatin, sorbitol, tragacanth gum, polyvinyl pyrrolidone or CMC-Ca, an excipient such as lactose, sugar, corn starch, calcium phosphate, sorbitol, glycine or crystal cellulose powder, a lubricant such as magnesium stearate, talc, polyethylene glycol or silica, and a disintegrator such as potato starch.

However, the pharmaceutical composition of the present invention is not limited to such oral administration and it is applicable for parenteral administration. For example, it may be administered in the form of e.g. a suppository formulated by using oily base material such as cacao butter, polyethylene glycol, lanolin or fatty acid triglyceride, a transdermal therapeutic base formulated by using liquid paraffin, white vaseline, a higher alcohol, Macrogol ointment, hydrophilic ointment or hydro-gel base material, an injection formulation formulated by using one or more materials selected from the group consisting of polyethylene glycol, hydro-gel base material, distilled water, distilled water for injection and an excipient such as lactose or corn starch, or a formulation for administration through mucous membranes such as an ocular mucous membrane, a nasal mucous membrane and an oral mucous membrane.

Further, the compounds of the present invention may be combined with basic ion-exchange resins which are capable of binding bile acids and yet not being absorbed by the gastrointestinal tract.

The daily dose of the compound of the formula I is from 0.05 to 500 mg, preferably from 0.5 to 50 mg, for an adult. It is administered from once to three times per day. The dose may of course be varied depending upon the age, the weight of the condition of illness of the patient.

Now, the present invention will be described in further detail with reference to Examples showing the inhibitory effects of the compounds of the present invention against atherosclerotic intimal thickening. The chemical structures of the tested compounds of the present invention (Test Compounds 1 to 3) and comparative compounds (Pravastatin as disclosed in Japanese Unexamined Patent Publication No. 185275/1982 or EP65835, and Simvastatin as disclosed in Japanese Unexamined Patent Publication No. 122373/1981 or EP33536) are as follows:

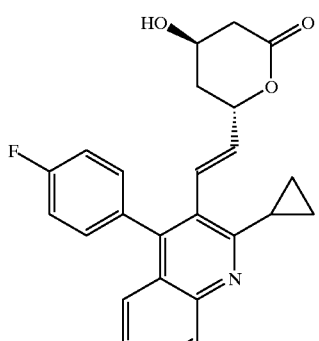

Test compound 1

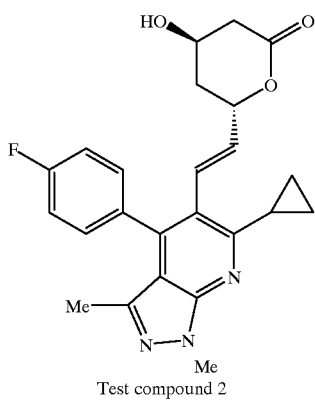

Test compound 2

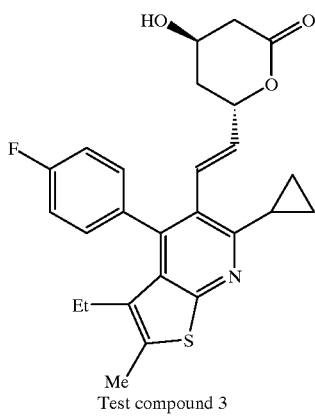

Test compound 3

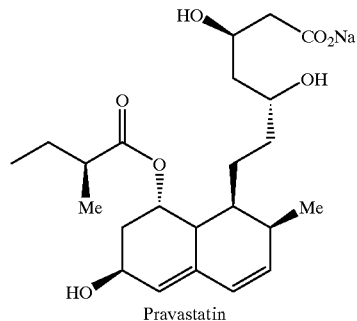

Pravastatin

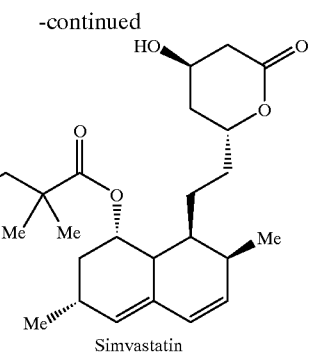

Simvastatin

REFERENCE EXAMPLE (E)-trans-6-(2'-[4"-(4'''-(fluorophenyl)-1''',3''-dimethyl-6''-(1'''-methylethyl)pyrazolo[3,4-b]pyridin-5''-yl)ethenyl)4-hydroxy-3,4,5,6-tetrahydro-2H-pyran-2-one
(Compound I-3b-1)

This compound was prepared using methyl 2-cyclopropyl-5-ethyl-3-(4'-fluorophenyl)-6-methylthieno[2,3-b]pyridin-3-ylcarboxylate (Compound VIIb-1) as the starting material through the following Steps A to H.

In a similar manner, test compounds 1, 2 and 3 were prepared from the following intermediates (VIIa-1, VIIb-2 and VIIc-1):

Compound VIIa-1
Methyl 2-cyclopropyl-4-(4'-fluorophenyl)quinolin-3-ylcarboxylate Compound VIIb-2
Methyl 6-cyclopropyl-1,3-dimethyl-4-(4'-fluorophenyl)pyrazolo[3,4-b]pyridin-5-ylcarboxylate Compound VIIc-1
Methyl 6-cyclopropyl-3-ethyl-4-[4'-fluorophenyl)-2-methylthieno[2,3-b]pyridin-5-ylcarboxylate.

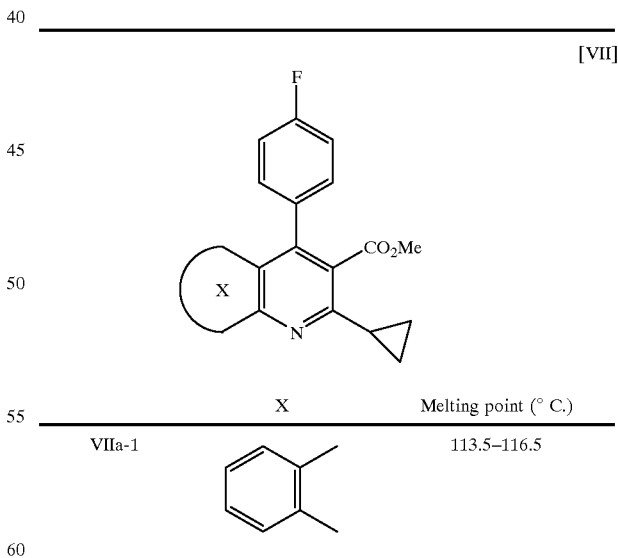

| X | Melting point (° C.) |
|---|---|
| VIIa-1 | 113.5–116.5 |

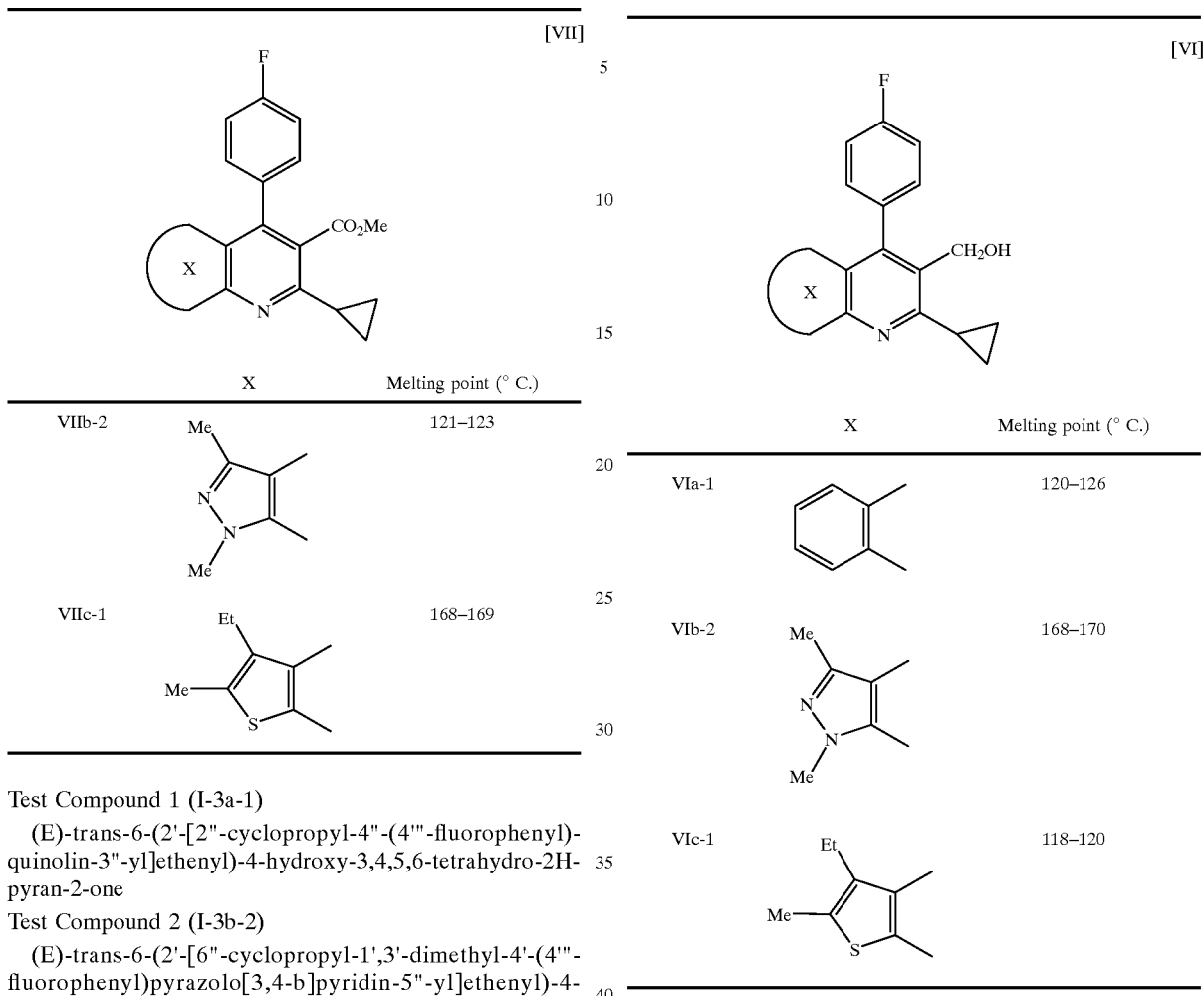

| | X | Melting point (° C.) |
|---|---|---|
| VIIb-2 | (Me, N-N(Me), Me pyrazole) | 121–123 |
| VIIc-1 | (Et, Me, Me thiophene) | 168–169 |

Test Compound 1 (I-3a-1)

(E)-trans-6-(2'-[2"-cyclopropyl-4"-(4'"-fluorophenyl)-quinolin-3"-yl]ethenyl)-4-hydroxy-3,4,5,6-tetrahydro-2H-pyran-2-one Test Compound 2 (I-3b-2)

(E)-trans-6-(2'-[6"-cyclopropyl-1',3'-dimethyl-4'-(4'"-fluorophenyl)pyrazolo[3,4-b]pyridin-5"-yl]ethenyl)-4-hydroxy-3,4,5,6-tetrahydro-2H-pyran-2-one Test Compound 3 (I-3c-1)

(E)-trans-6-(2'-[2'-cyclopropyl-5'-ethyl-3'-(4'"-fluorophenyl)-6'-methylthieno[2,3-b]pyridin-3'-yl]ethenyl)-4-hydroxy-3,4,5,6-tetrahydro-2H-pyran-2-one Step A 4-(4'-fluorophenyl)-5-hydroxymethyl-1,3-dimethyl-6-(1'-methylethyl)pyrazolo[3,4-b]pyridine (Compound VI-b-1)

Under a nitrogen atmosphere, 5.0 g (0.014 mol) of Compound VIIb-1 was dissolved in dry toluene and cooled to 0° C. in an ice bath. To this solution, 35 ml of a toluene solution containing 16% by weight of diisobutylaluminum hydride was dropwise added, and the mixture was stirred at 0° C. for 2 hours. After confirming by thin layer chromatography that Compound VIIb-1 completely disappeared, a saturated ammonium chloride solution was added at 0° C. to terminate the reaction. Ethyl ether was added to the reaction mixture, and the organic layer was separated. To a gelled substance, an aqueous sodium hydroxide solution was added to dissolve it, and the solution was extracted with ethyl ether. The ethyl ether extract was put together, dried over anhydrous magnesium sulfate and subjected to filtration, and the solvent was distilled off to obtain 3.9 g of a slightly yellow desired product. Yield: 88%, melting point: 174–175° C.

In a similar manner, the following compounds were prepared.

| | X | Melting point (° C.) |
|---|---|---|
| VIa-1 | (o-xylyl) | 120–126 |
| VIb-2 | (Me, N-N(Me), Me pyrazole) | 168–170 |
| VIc-1 | (Et, Me, Me thiophene) | 118–120 |

Step B (4-(4'-fluorophenyl)-1,3-dimethyl-6-(1'-methylethyl)pyrazolo[3,4-b]pyridin-5-yl)carboxyaldehyde (Compound Vb-1)

4.2 g (19 mmol) of pyridinium chlorochromate, 0.69 g of anhydrous sodium acetate and 3.8 g (12 mmol) of Compound VIb-1 were suspended in 50 ml of dry dichloromethane at room temperature. The reaction solution was stirred for one hour, and 100 ml of ethyl ether was added thereto and thoroughly mixed. The reaction mixture was filtered under suction through a cerite layer, and the filtrate was evaporated to dryness under reduced pressure. The residue was purified by silica gel column chromatography (eluent: chloroform) to obtain 2.9 g of a slightly yellow desired product. Yield: 78%, melting point: 144–146° C.

In a similar manner, the following compound were prepared.

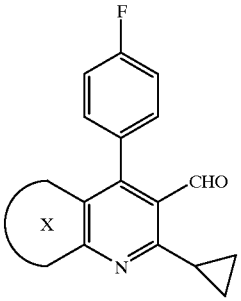

[V]

| | X | Melting point (° C.) |
|---|---|---|
| Va-1 | 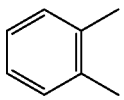 | 150.1–151.6 |
| Vb-2 | 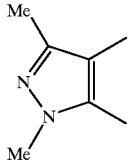 | 149–151 |
| Vc-1 | 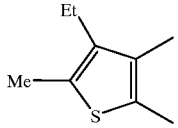 | 174–176 |

Steps C and D (E)-3-[4'-(4"-fluorophenyl)-1',3'-dimethyl-6'-(1"-methylethyl)pyrazolo[3,4-b]pyridin-5'-yl]propenealdehyde (Compound IIIb-1)

Step C 1.45 g (40 mmol) of cis-1-ethoxy-2-(tri-n-butylstannyl) ethylene was dissolved in 50 ml of dry tetrahydrofuran, and the solution was cooled to −78° C. under a nitrogen stream. To this solution, 26 ml (40 mmol) of a solution of 15 wt % of n-butyl lithium in n-hexane, was dropwise added. The mixture was stirred for 20 minutes. Then, a solution having 2.5 g (8 mmol) of Compound Vb-1 dissolved in 20 ml of dry tetrahydrofuran, was dropwise added thereto. The reaction mixture was stirred at −78° C. for one hour, and then 26 ml of a saturated ammonium chloride solution was added to terminate the reaction. The organic layer was extracted with diethyl ether, and the ether extract was washed with a saturated sodium chloride aqueous solution and dried over anhydrous magnesium sulfate. The solvent was distilled off under reduced pressure, and the residue was subjected to liquid separation between n-hexane and acetonitrile, and the acetonitrile layer was distilled under reduced pressure to distill the solvent off and to obtain substantially pure Compound IVb-1.

Step D

Compound IVb-1 obtained in Step C was dissolved in 70 ml of tetrahydrofuran, and 20 ml of water and 3 g of p-toluene sulfonic acid were added thereto. The mixture was stirred at room temperature for 2 hours. The reaction solution was carefully neutralized with an aqueous sodium hydroxide solution and then extracted a few times with diethyl ether. The extract was washed with a saturated sodium chloride aqueous solution and dried over anhydrous magnesium sulfate. Then, the solvent was distilled off under reduced pressure. The residue was purified by silica gel column chromatography (eluent: ethyl acetate/n-hexane=1/9 (v/v)) to obtain a yellow desired product. Amount: 2.2 g (yield: 79%), melting point: 133–134° C.

In the same manner, the following compounds were prepared.

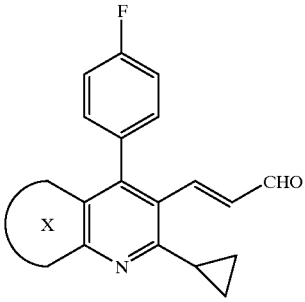

[III]

| | X | Melting point (° C.) |
|---|---|---|
| IIIa-1 | 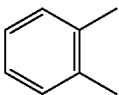 | 141.3–144.1 |
| IIIb-2 | 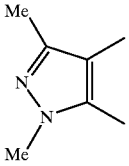 | 135–137 |
| IIIc-1 | 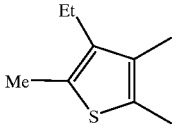 | 136–138 |

Step E

Ethyl (E)-7-[4'-(4"-fluorophenyl)-1',3'-dimethyl-6'-(1"-methylethyl)pyrazolo[3,4-b]pyridin-5-yl]-5-hydroxy-3-oxohept-6-enoate (Compound IIb-1)

1.25 g of 60% sodium hydride was washed with dried petroleum ether, dried under nitrogen stream and then suspended in 200 ml of dry tetrahydrofuran. The suspension was cooled to −15° C. in a nitrogen atmosphere, and 3.9 ml (30 mmol) of ethyl acetoacetate was dropwise added thereto. The mixture was stirred for 15 minutes. Then, 20 ml (30 mmol) of a solution of 15 wt % of n-butyl lithium in n-hexane was dropwise added thereto, and the mixture was stirred for 30 minutes. Further, a solution having 2.1 g (6.1 mmol) of Compound IIIb-1 dissolved in dry tetrahydrofuran, was dropwise added thereto, and the mixture was stirred for one hour. To the reaction mixture, 10 ml of a saturated ammonium chloride aqueous solution was added at −15° C., and the mixture was extracted three times with diethyl ether. The ether solution was washed with a saturated sodium chloride aqueous solution and dried over anhydrous magnesium sulfate, and then it was evaporated to dryness under reduced pressure. The residue was purified by silica gel column chromatography (eluent: ethyl acetate/chloroform=1/9 (v/v)) to obtain 2.5 g (yield: 89%) of a white desired product. Melting point: 95–98° C.

In the same manner, the following compounds were prepared.

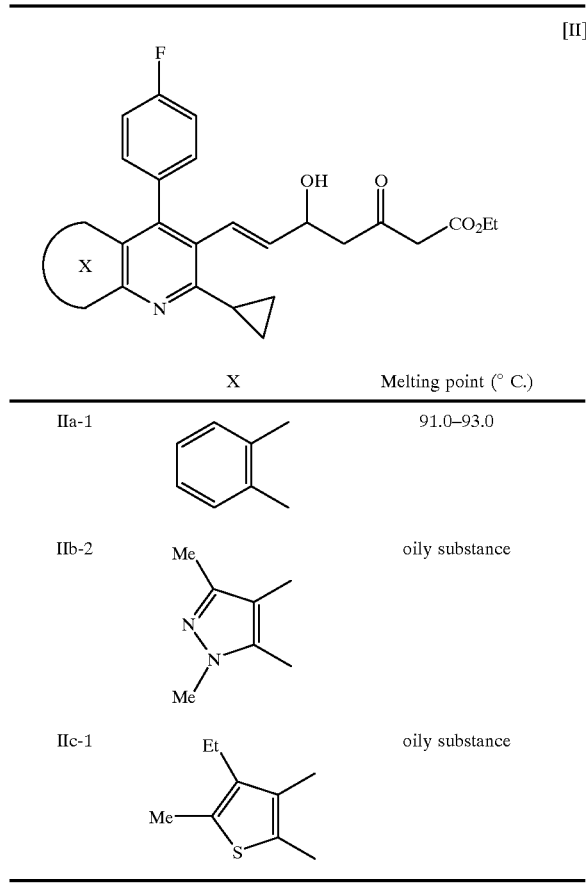

Step F

Ethyl (E)-7-[4'-(4"-fluorophenyl)-1',3'-dimethyl-6'-(1"-methylethyl)pyrazolo(3,4-b]pyridin-5'-yl]-3,5-dihydroxyhept-6-enoate (Compound I-1b-1)

Under a nitrogen atmosphere, 2.32 g (4.96 mmol) of Compound IIb-1 was dissolved in 20 ml of ethanol, and the solution was cooled to 0° C. Then, 740 mg (20 mmol) of sodium borohydride was added thereto, and the mixture was stirred for one hour. A 10% hydrochloric acid aqueous solution was added thereto to carefully neutralize the mixture. Then, the mixture was extracted three times with ethyl ether. The ether solution was washed with a saturated sodium chloride aqueous solution and dried over anhydrous magnesium sulfate, and then it was evaporated to dryness under reduced pressure. The residual oil was purified by silica gel column chromatography (eluent: ethanol/chloroform=3/97 (v/v)) to obtain a pure desired product as a colorless viscous oil. Amount: 1.81 g (yield: 78%)

NMR(δppm CDCl$_3$) 1.28(t,J=8 Hz,3H), 1.32(d,J=8 Hz,6H), 1.4–1.8(m,1H), 1.92(s,3H), 2.2–2.6(m,3H), 2.9–3.8 (m,2H), 3.42(7 heptalet, J=8 Hz,1H), 4.06(s,3H), 4.1–4.6 (m,4H), 5.1–5.5(m,1H), 6.4–6.7(m,1H), 6.9–7.3(m,4H)

In the same manner, the following compounds were prepared.

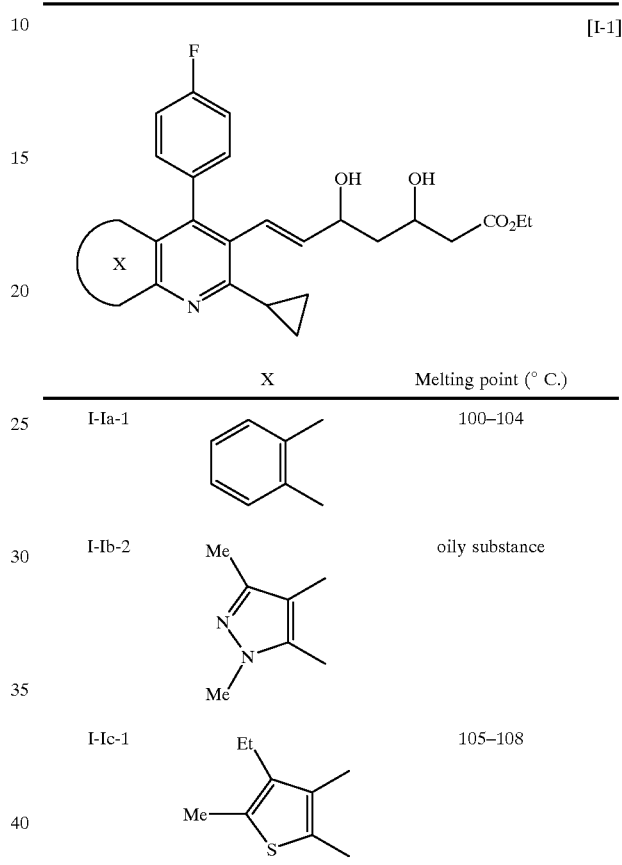

Step G

Sodium salt of (E)-7-[4'-(4"-fluorophenyl)1',3'-dimethyl-6'-(1"-methylethyl)pyrazolo[3,4-b]pyridin-5'-yl]-3,5-dihydroxyhept-6-enoic acid (Compound I-5b-1)

200 mg (0.43 mmol) of Compound I-1b-1 was dissolved in 2 ml of ethanol, and 0.85 ml of a 0.5N sodium hydroxide aqueous solution was dropwise added thereto. The mixture was further stirred at room temperature for one hour. Then, ethanol was distilled off under reduced pressure, and 2 ml of water was added to the residue. Then, the mixture was extracted with ethyl ether. The aqueous layer was freeze-dried to obtain 180 mg (91%) of a hygroscopic slightly yellow powder. Melting point:

258–264° C. (decomposed).

In the same manner, the following compounds were prepared.

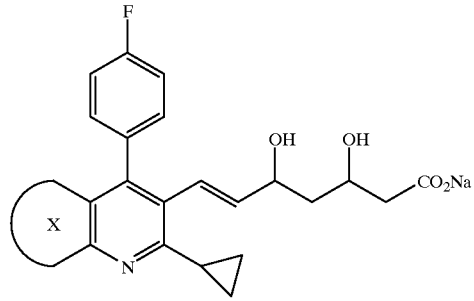

[I-5]

| X | | Melting point (° C.) |
|---|---|---|
| I-5a-1 | 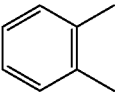 | 197–199 (decomposed) |
| I-5b-2 | 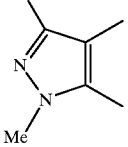 | 230–237 (decomposed) |
| I-5c-1 | 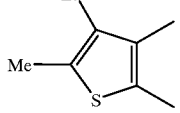 | 212–216 (decomposed) |

(E)-7-[4'-(4"-fluorophenyl)-1',3'-dimethyl-6'-(1"-methylethyl)pyrazolo[3,4-b]pyridin-5'-yl]-3,5-dihydroxyhept-6-enoic acid (Compound I-2b-1)

0.25 g (0.53 mmol) of Compound I-1b-1 was dissolved in 3 ml of ethanol, and 1.06 ml of a 0.5N sodium hydroxide aqueous solution was dropwise added thereto. Ethanol was distilled off under reduced pressure, and then 3 ml of distilled water was added to the residue. And the mixture was extracted with ethyl ether. The aqueous layer was carefully neutralized with 1% hydrochloric acid and then extracted with ethyl ether. The ether layer was dried over anhydrous magnesium sulfate and then distilled under reduced pressure to obtain the desired product. Amount: 0.21 g (yield: 90%)

P-NMR(DMSO-d$^6$) δppm: 1.29(d,J=7 Hz,6H), 1.83(s, 3H), 2.1–2.3(m,2H), 2.4–2.6(m,1H), 3.0–3.6(m,4H), 3,96(s, 3H), 4.3–4.8(m,2H), 5.2–5.6(m,1H), 6.3–6.6(m,1H), 7.2–7.4(m,4H), 11.5–12.0(bs,1H)

Step H (E)-trans-6-(2'-[4"-(4'"-fluorophenyl)-1',3'-dimethyl-6"-1'"-methylethyl)pyrazolo[3,4-b]pyridin-5"-yl]ethenyl)-4-hydroxy-3,4,5,6-tetrahydro-2H-pyran-2-one (Compound I-3b-1)

130 mg (0.29 mmol) of Compound I-2b-1 was dissolved in 6 ml of dichloromethane, and 125 mg (0.29 mmol) of N-cyclohexyl-N'-(2"-methylmorpholinoethyl)carbodiimide p-toluenesulfonate was added thereto. The mixture was stirred at room temperature for 2 hours, and the solvent was distilled off under reduced pressure to dryness. The residual oil was purified by silica gel thin layer chromatography (eluent: hexane/ethyl acetate=9/1 (v/v)) to obtain a pure desired product as a colorless viscous oil. Amount: 48 mg (yield: 39%)

P-NMR(CDCl$_3$) δppm:
1.33(d,J=6.8 Hz,6H), 1.4–1.5(m,1H), 1.6–1.7(m,2H), 1.93(s,3H), 2.5–2.6(m,1H), 2.68(dd,J=18 Hz,J=5 Hz,1H), 3.39(7 heptalet,J=6.8 Hz,1H), 4.07(s,3H), 4.1–4.2(m,1H), 5.1–5.2(m,1H), 5.31(dd,J=16 Hz,J=6 Hz,1H), 6.61(dd,J=16 Hz,J=1.5 Hz,1H), 7.1–7.3(m,4H)

In the same manner, the following compounds were prepared.

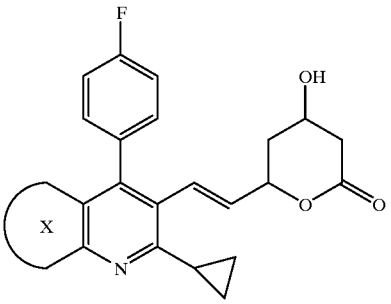

[I-3]

| X | | Melting point (° C.) |
|---|---|---|
| I-3a-1 | 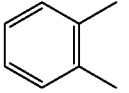 | 199–201 |
| I-3b-2 | 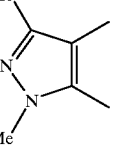 | 122–127 |
| I-3c-1 | 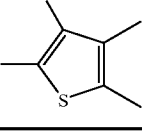 | 164–166 |

Example 1

The inhibitory effects on migration of aortic medial smooth muscle cells (M-SMC)

The inhibitory effects of the compounds of the present invention on migration of M-SMC were measured by the following methods.

Arterial medial slices of the thoracic of aorta of a Sprague Dawley male rat were cultured by using a medium of Dulbecco's Modified Eagle (DME) containing 10% fetal bovine serum (FBS) at 37° C. in an atmosphere comprising 95% of air and 5% of carbon dioxide for 3 or 4 weeks. The aortic medial smooth muscle cells grown from the arterial medial slices were subcultured by 1:2 split of cell density for stable subculture. After the three or four times subculture, the cells in the state of confluency were subjected to trypsinized and then suspended in the above medium at a cell density of 500,000 cells per ml. To the cell suspension, a test compound dissolved in dimethylsulfoxide (DMSO) was added so that the final DMSO concentration would be 0.2%, and the cell suspension was pre-incubated at 37° C. for 30 minutes. As a control, DMSO was added alone at the same concentration. In the lower compartment of Boyden's chamber partitioned with a nitrocellulose membrane, 10 ng/ml of a platelet-derived growth factor (PDGF) or DME medium containing a 10% SMC-conditioned DME medium (SMC-CM) obtained from 48 hours conditioning was filled as a migration factor. In the upper compartment thereof, 1 ml of the cell suspension was loaded, and incubation was conducted at 37° C. for 4 hours in a culture condition. As the blank, the DME medium without migration factor was filled in the lower compartment. After 4 hour incubation, the cells adhered to the upper side of the nitrocellulose membrane were removed, and the cells migrated to the lower side of the membrane were fixed and stained by Diff Quik. The number of migrated cells was counted in the 10 fields by a light microscope at 400 x HPF.

The obtained results were represented by an average value of cell numbers of three chambers in each case, and the inhibition (%) was calculated in accordance with the following formula:

$$\text{Inhibition}(\%) = 100 - \{(T-B)/(C-B) \times 100\}$$

where B: cell number of the blank, C: cell number of the control, and T: cell number where a test compound is contained.

The results are shown in Table 5. The compounds of the present invention showed strong inhibitory effects against migration of M-SMC as compared with the comparative compound.

TABLE 5

| Drug Concentration (M) | Inhibition (%) | |
|---|---|---|
| | PDGF $10^{-5}$ | SMC-CM $10^{-5}$ |
| Test compound 1 | 77.8 | 28.4 |
| Test compound 2 | 98.2 | 32.8 |
| Test compound 3 | 100 | 41.7 |
| Pravastatin | 61.8 | 26.2 |

Example 2

The inhibitory effects on the proliferation of aortic intimal and medial smooth muscle cells (I-SMC and M-SMC)

The inhibitory effects of the compounds of the present invention on the proliferation of I-SMC and M-SMC were measured by the following methods.

Using a DME medium containing 10% of FBS and an antibiotic, slices of aortic media obtained from, a healthy Japanese white rabbit and slices of aortic intimal lesion separated from media of aorta obtained from an atherosclerotic Japanese white rabbit fed a 1% cholesterol diet for 3 months were cultured in the same manner as in Example 1. After twice or three times subculture of cells, the cells in the state of confluency were trypsinized and suspended in the above medium so that the cell density would be 20,000 cells/ml. Then, the 10,000 cells were seeded and cultured on a 24 well multi-well plate. After incubation for 6 hours, the medium was replaced by 0.5 ml of a control medium or a medium containing a test compound. At the same time, the number of cells initially attached to the plate was counted and taken as the initial cell number (I). The test compound was added to the medium as described in Example 1. As the control, DMSO was added alone so that the final concentration would be 0.2%. The medium change was carried out every 2 days, and on the first, second, third, fifth and seventh days, the cells were trypsinized and suspended in Isoton and counted cell number by a Coulter counter.

The obtained results were represented by an average number of cells of three wells in each case, and the inhibition (%) of the fold increase of the cell number from the second day to the fifth day was calculated in accordance with the following formula.

$$\text{Inhibition}(\%) = 100 - \{(T_5/T_2)/(C_5/C_2) \times 100\}$$

where $T_2$ and $T_5$ are the cell number on the second day and the fifth day, respectively, in the medium containing the test compound, and $C_2$ and $C_5$ are the number of cells on the second day and the fifth day, respectively, in the control medium.

The results are shown in Table 6, the compounds of the present invention showed strong inhibitory effects on the proliferation of both I-SMC and M-SMC as compared with the comparative compound. Further, the inhibitory effect on the I-SMC proliferation was higher in its effects than on the M-SMC proliferation.

TABLE 6

| | Inhibition (%) | | | |
|---|---|---|---|---|
| | Intima | | Media | |
| Drug Concentration (M) | $10^{-6}$ | $10^{-5}$ | $10^{-6}$ | $10^{-5}$ |
| Test compound 1 | 36.4 | 98.1 | 6.3 | 91.5 |
| Test compound 2 | 84.6 | 98.2 | 4.7 | 86.5 |
| Test compound 3 | 100 | 100 | 31.5 | 100 |
| Pravastatin | 1.3 | 1.3 | 8.7 | −11.7 |

Example 3

The inhibitory effect on $^3$H-thymidine uptake in aortic intimal and medial smooth muscle cells (I-SMC and M-SMC)

The inhibitory effects of the compound of the present invention on $^3$H-thymidine uptake in I-SMC and M-SMC were measured by the following methods.

M-SMC and I-SMC are obtained from aortic media of a healthy Japanese white rabbit and from aortic intima of an atherosclerotic Japanese white rabbit as mentioned in Example 2. After three or four times subculture, the cells in the state of confluency were trypsinized and suspended in a DME medium containing 10% of FBS and an antibiotic so that the cell density would be 40,000 cells/ml. The 10,000 cells were seeded to a 48 well multi-well plate. After 4 days culture, the medium was replaced by the control medium or the medium containing a test compound as used in Example 2, and culture was continued for 24 hours. Then, 1 μCi (37 MBq) of $^3$H-thymidine was added thereto, and culture was continued for 3 hours. The cells were washed three times with a phosphate buffered physiological saline (PBS) and treated with chilled 5% trichloroacetic acid (TCA). The insoluble-fraction was washed with chilled TCA and then dissolved in a 0.5N potassium hydroxide aqueous solution. The $^3$H radioactivity was measured by a liquid scintillation counter and the protein content was measured.

The obtained results were calculated as the radioactivity per 1 mg of protein and represented as an average value of 3 wells. The inhibition (%) was calculated in accordance with the following formula.

$$\text{Inhibition}(\%) = 100 - T/C \times 100$$

The results are shown in Table 7. The compounds of the present invention showed strong inhibitory effects on $^3$H-thymidine uptake into DNA fraction in intimal and medial smooth muscle cells, as compared with the comparative compound.

TABLE 7

| Drug Concentration (M) | Inhibition (%) | | | |
|---|---|---|---|---|
| | Intima | | Media | |
| | $10^{-6}$ | $10^{-5}$ | $10^{-6}$ | $10^{-5}$ |
| Test compound 1 | 32.2 | 83.1 | 46.7 | 90.8 |
| Test compound 2 | 11.7 | 91.5 | 36.4 | 88.4 |
| Test compound 3 | 69.9 | 94.1 | 53.6 | 92.2 |
| Pravastatin | −7.0 | −7.2 | 8.7 | −34.3 |

Example 4

The inhibitory effects against adhesion of leukemic cells (HL-60)

The inhibitory effects of the compounds in the present invention on cell adhesion of HL-60 were measured by the following methods. HL-60 cells were cultured in a RPMI 1640 medium containing 10% of FBS and an antibiotic at 37° C. in an atmosphere comprising 95% of air and 5% of carbon dioxide and then seeded to a 6 well multi-well plate in an amount of 2 ml per well at a cell density of 1,000,000/ml. A test compound dissolved in DMSO was added so that the final DMSO concentration would be 0.2%, and incubation was carried out for 48 hours for pretreatment. Then, 500,000 cells were seeded to a 24 well multi-well plate, and 0.02 mM of phorbol myristate acetate (TPA) dissolved in ethanol, was added in an amount of 1/250 (v/v) of the culture medium, and then culture was continued for 12 hours. After that, the cells were washed with PBS and the cells attached to the well plates were scraped off by trypsinization and suspended in Isoton, and the number of cells were counted by a Coulter counter. A control test was carried out by adding DMSO alone.

The obtained results were represented by an average value of the number of cells in three wells at the time of the pretreatment, and the inhibition (%) was calculated in accordance with the following formula:

Inhibition (%) against adhesion=$100-T/C\times100$ where T: number of cells in the medium containing a test compound C: number of cells in the control medium.

The results are shown in Table 8. The compounds of the present invention showed distinctly strong inhibitory effects on cell adhesion of HL-60 induced by TPA, as compared with the comparative compound.

TABLE 8

| Drug Concentration (M) | Inhibition (%) | | |
|---|---|---|---|
| | $10^{-7}$ | $10^{-6}$ | $10^{-5}$ |
| Test compound 1 | 1.0 | 12.3 | 98.7 |
| Test compound 3 | 4.8 | 92.2 | 96.4 |
| Pravastatin | | | −2.8 |

Example 5

The inhibitory effects against adhesion of J774 macrophages (J774-Mφ)

The inhibitory effects of the compounds in the present invention on cell adhesion of J774-Mφ were measured by the following methods.

1,000,000 cells were seeded to a 6 well multi-well plate, and cultured in 1 ml of a DME medium containing 10% of FBS and an antibiotic at 37° C. in an atmosphere comprising 95% of air and 5% of carbon dioxide for 2 days. Then, culture was continued with a control medium containing 0.2% of DMSO or with a medium containing a test compound for 48 hours as pretreatment. Then, the cells were scraped by means of a rubber policeman and suspended in the above medium. 200,000 cells were seeded to a 24 well multi-well plate., and cultured for 12 hours. After that, the cells attached to the well plates were scraped by a rubber policeman, and the number of cells was counted by a Coulter counter.

The obtained results are represented by an average value of the number of cells in three wells at the time of the pretreatment, in each case, and the inhibition (%) on the adhesion was calculated in accordance with the following formula.

Inhibition (%) against adhesion=$100-T/C\times100$ where T: number of cells in the medium containing a test compound C: number of cells in the control medium.

The results are shown in Table 9. The compounds of the present invention showed strong inhibitory effects against cell adhesion of J774-Mφ.

TABLE 9

| Drug Concentration (M) | Inhibition (%) | |
|---|---|---|
| | $10^{-6}$ | $10^{-5}$ |
| Test compound 1 | 53.0 | 74.2 |
| Test compound 3 | 92.2 | 92.4 |
| Pravastatin | 40.0 | 41.3 |
| Simvastatin | 48.5 | 48.6 |

The compounds of the present invention have inhibitory effects on HMG-CoA reductase and inhibit atherosclerotic intimal thickening, and thus they are useful as preventive drugs for coronary heart diseases such as angina pectoris, myocardial infarction, re-athenosis after PTCA, cerebrovascular contraction after sabarachnoid hemorrhage and obliterating sclerosing arteritis.

What is claimed is:

1. A method for inhibiting re-athenosis after PTCA, cerebrovascular contraction after subarachnoid hemorrhage and obliterating sclerosing arteritis, comprising administering to a patient in need thereof an effective amount of a compound of the formula

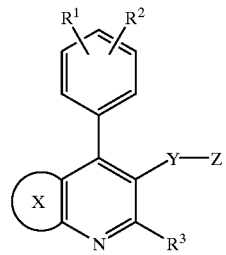

(I)

wherein ring X is phenyl, substituted phenyl or 5- or 6-membered heterocyclic aryl;

$R^1$ and $R^2$ are, independently, hydrogen, $C_{1-8}$ alkyl, $C_{3-7}$ cycloalkyl, $C_{1-3}$ alkoxy, n-butoxy, i-butoxy, sec-butoxy, tert-butoxy, $R^{20}R^{21}N$-, trifluoromethyl, trifluoromethoxy, difluoromethoxy, fluoro, chloro, bromo, phenyl, phenoxy, benzyloxy, hydroxy, trimethylsilyloxy, diphenyl-tert-butylsilyloxy, hydroxymethyl or —O(CH$_2$)$_l$OR$^{22}$, where each of R$^{20}$ and R$^{21}$ is, independently, hydrogen or C$_{1-3}$ alkyl, R$^{22}$ is hydrogen or C$_{1-3}$ alkyl, and l is 1, 2, or 3; or R$^1$ and R$^2$ together form —CH=CH—CH=CH— or methylenedioxy, when they are at the o-position to each other;

R$^3$ is hydrogen, C$_{1-8}$ alkyl, C$_{2-6}$ alkenyl, C$_{3-7}$ cycloalkyl, C$_{5-7}$ cyloalkenyl or

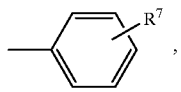, where R$^7$ is hydrogen, C$_{1-8}$ alkyl, C$_{1-8}$ alkoxy, C$_{1-3}$ alkylthio, chloro, bromo, fluoro, chloromethyl, trichloromethyl, trifluoromethyl, trifluoromethoxy, trichloromethoxy, difluoromethoxy, phenoxy, benzyloxy, hydroxy, trimethylsilyloxy, diphenyl-tert-butylsilyloxy or hydroxymethyl; or C$_{1-3}$ alkyl substituted by

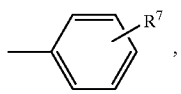, wherein R$^7$ is as defined above and zero, one or two C$_{1-3}$ alkyl;

Y is —CH$_2$—, —CH$_2$CH$_2$—, —CH=CH—, —CH$_2$—CH=CH—, —CH=CH—CH$_2$—, —C(CH$_3$)=CH— or —CH=C(CH$_3$)—;

Z is —Q—CH$_2$—W—CH$_2$—CO$_2$R$^{12}$,

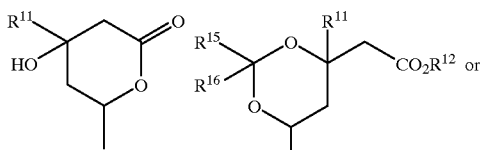

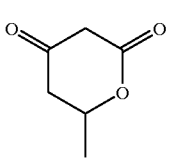

wherein Q is —C(O)—, —C(OR$^{13}$)$_2$— or —CH(OH)—,

W is —C(O)—, —C(OR$^{13}$)$_2$— or —C(R$^{11}$)(OH)—,

R$^{11}$ is hydrogen or C$_{1-3}$ alkyl,

R$^{12}$ is hydrogen, alkyl of a chemically or physiologically hydrolyzable alkyl ester moiety, NHR$^{23}$R$^{24}$R$^{25}$, sodium, potassium or ½ calcium, where each of R$^{23}$, R$^{24}$ and R$^{25}$ is independently hydrogen or C$_{1-4}$ alkyl, each R$^{13}$ is independently a primary or secondary C$_{1-6}$ alkyl, or two R$^{13}$ together form —(CH$_2$)$_2$— or —(CH$_2$)$_3$—, and each of R$^{15}$ and R$^{16}$ is independently a hydrogen atom or C$_{1-3}$ alkyl, or R$^{15}$ and R$^{16}$ together form —(CH$_2$)$_2$— or —(CH$_2$)$_3$—.

2. The method of claim 1, wherein said compound is administered orally or parenterally.

3. The method of claim 2, wherein said effective amount is from 0.05 to 500 mg per day.

4. The method of claim 3, wherein said effective amount is from 0.5 to 50 mg per day.

5. The method of claim 3, wherein said compound is administered from one to three times per day.

6. The method of claim 1, wherein the compound is of the formula (Ia):

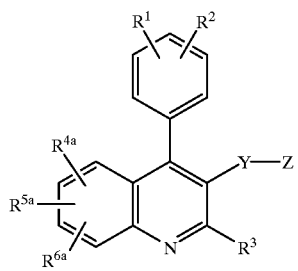

wherein each of R$^{4a}$, R$^{5a}$ and R$^{6a}$ is, independently, hydrogen, C$_{1-6}$ alkyl, C$_{3-7}$ cycloalkyl, C$_{1-3}$ alkoxy, n-butoxy, i-butoxy, sec-butoxy, R$^{26}$R$^{27}$N-, trifluoromethyl, trifluoromethoxy, difluoromethoxy, fluoro, chloro, bromo, phenyl, phenoxy, benzyloxy, hydroxy, trimethylsilyloxy, diphenyl-tert-butylsilyloxy, hydroxymethyl or —O(CH$_2$)$_m$OR$^{28}$, wherein each of R$^{26}$ and R$^{27}$ is independently hydrogen or C$_{1-3}$ alkyl, R$^{28}$ is hydrogen or C$_{1-3}$ alkyl, and m is 1, 2 or 3; or R$^{4a}$ and R$^{5a}$ together from —CH=CH—CH=CH—; or R$^{4a}$ and R$^{5a}$ together form —OC(R$^{29}$)(R$^{30}$)O— when they are at the o-position to each other, wherein each of R$^{29}$ and R$^{30}$ is independently hydrogen or C$_{1-3}$ alkyl;

R$^1$ and R$^2$ are independently hydrogen, C$_{1-8}$ alkyl, C$_{3-7}$ cycloalkyl, C$_{1-3}$ alkoxy, n-butoxy, i-butoxy, sec-butoxy, tert-butoxy, R$^{20}$R$^{21}$N-, trifluoromethyl, trifluoromethoxy, difluoromethoxy, fluoro, chloro, bromo, phenyl, phenoxy, benzyloxy, hydroxy, trimethylsilyloxy, diphenyl-tert-butylsilyloxy, hydroxymethyl or —O(CH$_2$)$_l$OR$^{22}$, where each of R$^{20}$ and R$^{21}$ is independently hydrogen or C$_{1-3}$ alkyl, R$^{22}$ is hydrogen or C$_{1-3}$ alkyl, and l is 1, 2, or 3; or R$^1$ and R$^2$ together form —CH=CH—CH=CH— or methylenedioxy, when they are at the o-position to each other;

R$^3$ is hydrogen, C$_{1-8}$ alkyl, C$_{2-6}$ alkenyl, C$_{3-7}$ cycloalkyl, C$_{5-7}$ cycloalkenyl or

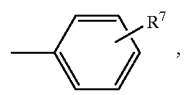, where R$^7$ is hydrogen, C$_{1-8}$ alkyl, C$_{1-8}$ alkoxy, C$_{1-3}$ alkylthio, chloro, bromo, fluoro chloromethyl, trichloromethyl, trifluoromethyl, trifluoromethoxy, trichloromethoxy, difluoromethoxy, phenoxy, benzyloxy, hydroxy, trimethylsilyloxy, diphenyl-tert-butylsilyloxy or hydroxymethyl; or C$_{1-3}$ alky substituted by

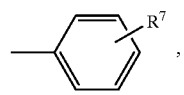, wherein R$^7$ is as defined above and zero, one or two C$_{1-3}$ alkyl;

Y is —CH$_2$—, —CH$_2$CH$_2$—, —CHH=CH—, —CH$_2$—CH=CH—, —CH=CH—CH$_2$—, —C(CH$_3$)=CH— or —CH=C(CH$_3$)—;

Z is —Q—CH$_2$—W—CH$_2$—CO$_2$R$^{12}$,

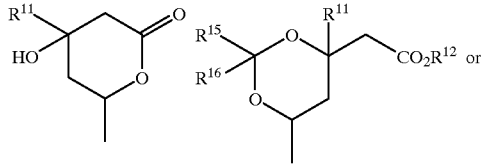

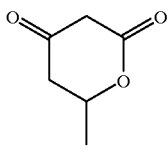

wherein Q is —C(O)—, —C(OR$^{13}$)$_2$— or —CH(OH)—,
W is —C(O)—, —C(OR$^{13}$)$_2$— or —C(R$^{11}$)(OH)—,
R$^{11}$ is hydrogen or C$_{1-3}$ alkyl,
R$^{12}$ is hydrogen, alkyl of a chemically or physiologically hydrolyzable alkyl ester moiety, NHR$^{23}$R$^{24}$R$^{25}$, sodium, potassium or ½ calcium, where each of R$^{23}$, R$^{24}$ and R$^{25}$ is independently hydrogen or C$_{1-4}$ alkyl,
each R$^{13}$ is independently a primary or secondary C$_{1-6}$ alkyl, or two R$^{13}$ together form —(CH$_2$)$_2$— or —(CH$_2$)$_3$—, and
each of R$^{15}$ and R$^{16}$ is independently a hydrogen atom or C$_{1-3}$ alkyl, or R$^{15}$ and R$^{16}$ together form —(CH$_2$)$_2$— or —(CH$_2$)$_3$—.

7. The method of claim 1, wherein the compound is of the formula (Ib):

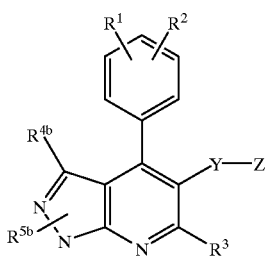 (Ib)

wherein R$^{4b}$ is hydrogen, C$_{1-8}$ alkyl, C$_{1-6}$ alkoxy, C$_{3-7}$ cycloalkyl, C$_{2-6}$ alkenyl, α- or β-naphthyl, 2-, 3- or 4-pyridyl, 2- or 3-thienyl, 2- or 3-furyl, fluoro, chloro, bromo, or

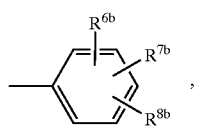

wherein each of R$^{6b}$, R$^{7b}$ and R$^{8b}$ is, independently, hydrogen, C, alkyl, C$_{1-8}$ alkoxy, C$_{1-3}$ alkylthio, chloro, bromo, fluoro, —NR$^{31}$R$^{32}$, chloromethyl, trichloromethyl, trifluoromethyl, trifluoromethoxy, trichloromethoxy, difluoromethoxy, phenoxy, benzyloxy, hydroxy, trimethylsilyloxy, diphenyl-tert-butylsilyloxy, hydroxymethyl or -O(CH$_2$)$_n$OR$^{33}$, wherein each of R$^{31}$ and R$^{32}$ is, independently, C$_{1-3}$ alkyl, R$^{33}$ is hydrogen or C$_{1-3}$ alkyl, and n is 1,2 or 3, or when R$^{8b}$ is hydrogen, R$^{6b}$ and R$^{7b}$ together form —OC(R$^{34}$)(R$^{35}$)O— when they are at the o-position to each other, wherein each of R$^{34}$ and R$^{35}$ is independently hydrogen or C$_{1-3}$ alkyl, or when R$^{7b}$ and R$^{8b}$ are simultaneously hydrogen R$^{6b}$ is

phenyl-C$_{2-3}$ alkenyl or C$_{1-3}$ alkyl substituted by one member selected from C$_{1-3}$ alkoxy, naphthyl and

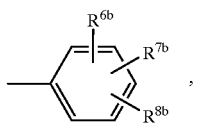

wherein R$^{36}$ is hydrogen, C$_{1-4}$ alkyl, C$_{1-3}$ alkoxy, trifluoromethyl, chloro, bromo or fluoro, the phenyl group of said phenyl-C$_{2-3}$ alkenyl may be substituted by C$_{1-4}$ alkyl, C$_{1-3}$ alkoxy, fluorine, chlorine or bromine, and R$^{6b}$, R$^{7b}$ and R$^{8b}$ are as defined above and zero, one or two C$_{1-3}$ alkyl;

R$^{5b}$ is bonded to a nitrogen atom at the 1- or 2-position of the pyrazolopyridine ring, and is hydrogen, C$_{1-8}$ alkyl, C$_{1-3}$ alkyl substituted by from one to three fluorine atoms, C$_{3-7}$ cycloalkyl, α- or β-naphthyl, 2-, 3- or 4-pyridyl, 2- or 3- thienyl, 2- or 3-furyl or

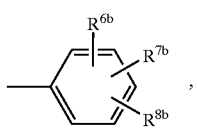

wherein R$^{6b}$, R$^{7b}$ and R$^{8b}$ are as defined above; or

C$_{1-3}$ alkyl substituted by one member selected from C$_{1-3}$ alkoxy, hydroxy, naphthyl and

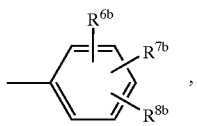

wherein R$^{6b}$, and R$^{7b}$ and R$^{8b}$ are as defined above and zero, one or two C$_{1-3}$ alkyl; and R$^1$ and R$^2$ are independently hydrogen, C$_{1-8}$ alkyl, C$_{3-7}$ cycloalkyl, C$_{1-3}$ alkoxy, n-butoxy, i-butoxy, sec-butoxy, tert-butoxy, R$^{20}$R$^{2"}$N-, trifluoromethyl, trifluoromethoxy, difluoromethoxy, fluoro, chloro, bromo, phenyl, phenoxy, benzyloxy, hydroxy, trimethylsilyloxy, diphenyl-tert-butylsilyloxy, hydroxymethyl or -O(CH$_2$)$_Q$OR$^{22}$, where each of R$^{20}$ and R$^{21}$ is independently hydrogen or C$_{1-3}$ alkyl, R$^{22}$ is hydrogen or C$_{1-3}$ alkyl, and Q is 1, 2, or 3; or R$^1$ and R$^2$ together form —CH=CH—CH=CH- or methylenedioxy, when they are at the o-position to each other;

R$^3$ is hydrogen, C$_{1-8}$ alkyl, C$_{2-6}$ alkenyl, C$_{3-7}$ cycloalkyl, C$_{5-7}$ cycloalkenyl or

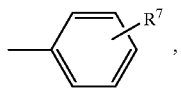

where $R^7$ is hydrogen, $C_{1-8}$ alkyl, $C_{2-6}$ alkoxy, $C_{1-3}$ alkylthio, chloro, bromo, fluoro, chloromethyl, trichloromethyl, trifluoromethyl, trifluoromethoxy, trichloromethoxy, difluoromethoxy, phenoxy, benzyloxy, hydroxy, trimethylsiyloxy, diphenyl-tert-butylsilyloxy or hydroxymethyl; or $C_{1-3}$ alky substituted by

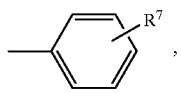

wherein $R^7$ is as defined above and zero, one or two $C_{1-3}$ alkyl;

Y is —CH$_2$—, —CH$_2$CH$_2$—, —CH=CH—, —CH$_2$—CH=CH—, —CH=CH—CH$_2$—, —C(CH$_3$)=CH— or —CH=C(CH$_3$)—;

Z is —Q—CH$_2$—W—CH$_2$—CO$_2$R$^{12}$,

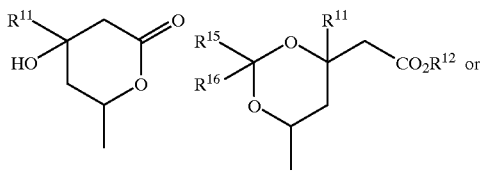

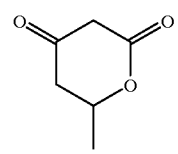

wherein Q is —C(O)—, —C(OR$^{13}$)$_2$— or —CH(OH)—,

W is —C(O)—, —C(OR$^3$)$_2$— or —C(R$^{11}$)(OH)—,

R$^{11}$ is hydrogen or $C_{1-3}$ alkyl,

R$^{12}$ is hydrogen, alkyl of a chemically or physiologically hydrolyzable alkyl ester moiety, NHR$^{23}$R$^{24}$R$^{25}$, sodium, potassium or ½ calcium, where each of R$^{23}$, R$^{24}$ and R$^{25}$ is independently hydrogen or $C_{1-4}$ alkyl, each R$^{13}$ is independently a primary or secondary $C_{1-6}$ alkyl, or two R$^{13}$ together form —(CH$_2$)$_2$— or —(CH$_2$)$_3$—, and each of R$^{15}$ and R$^{16}$ is independently a hydrogen atom or $C_{1-3}$ alkyl, or R$^{15}$ and R$^{16}$ together form —(CH$_2$)$_2$— or —(CH$_2$)$_3$—.

8. The method of claim 1, wherein the compound is of the formula (Ic):

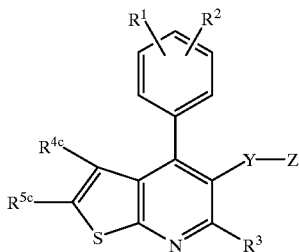

(Ic)

wherein each of R$^{4c}$ and R$^{5c}$ is independently hydrogen, $C_{1-8}$ alkyl, $C_{2-6}$ alkenyl, $C_{3-7}$ cycloalkyl, $C_{1-6}$ alkoxy, fluoro, chloro, bromo,

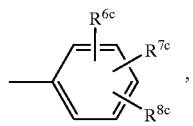

2-, 3- or 4-pyridyl, 2- or 5-pyrimidyl, 2- or 3-thienyl, 2- or 3 fury

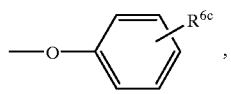

NR$^{37}$R$^{36}$, $C_{1-3}$ substituted by

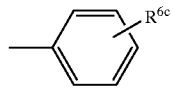

and zero, one or two $C_{1-3}$ alkyl, or α- or β-naphthyl; wherein each of R$^{6c}$, R$^{7c}$ and R$^{8c}$ is independently hydrogen, $C_{1-4}$ alkyl, $C_{1-3}$ alkoxy, $C_{3-7}$ cycloalkyl, trifluoromethyl, fluoro, chloro or bromo, and each of R$^{37}$ and R$^{38}$ is independently hydrogen, $C_{1-4}$ alkyl, or

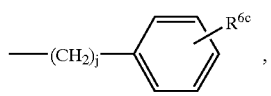

wherein R$^{6c}$ is as defined above and j is 1, 2 or 3, or R$^{37}$ and R$^{38}$ together form —(CH$_2$)$_k$—, wherein k is 3, 4 or 5, or R$^{4c}$ and R$^{5c}$ together form $C_{2-6}$ alkylene substituted by from zero to three members selected from the group consisting of $C_{1-4}$ alkyl, $C_{3-7}$ cycloalkyl, fluoro, chloro and bromo and from zero to one member selected from the group consisting of

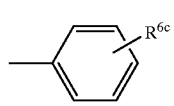

or —(CHR$^{39}$)$_p$—A—(CHR$^{40}$)$_q$—, wherein each of p and q is 0, 1, 2 or 3, A is —C(R$^{41}$)=C(R$^{42}$)—, —O—, —S—, —N(R$^{43}$)—, or —CH=CH—CH=CH—, wherein each of R$^{39}$ and R$^{40}$ is independently hydrogen or $C_{1-4}$ alkyl, each of $R^{41}$ and $R^{42}$ is hydrogen or $C_{1-3}$ alkyl, $R^{43}$ is hydrogen, $C_{1-4}$ alkyl, or

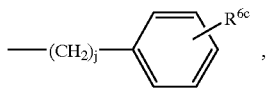

where $R^{6c}$ and j are defined as above; and $R^1$ and $R^2$ are independently hydrogen, $C_{1-4}$ alkyl, $C_{3-7}$ cycloalkyl, $C_{1-3}$ alkoxy, n-butoxy, i-butoxy, sec-butoxy, tert-butoxy, $R^{20}R^{21}N-$, trifluoromethyl, trifluoromethoxy, difluoromethoxy, fluoro, chloro, bromo, phenyl, phenoxy, benzyloxy, hydroxy, trimethylsilyloxy, diphenyl-tert-butylsilyloxy, hydroxymethyl or $-O(CH_2)_cOR^{22}$, where each of $R^{20}$ and $R^{21}$ is independently hydrogen or $C_{1-3}$ alkyl, $R^{22}$ is hydrogen or $C_{1-3}$ alkyl, and C is 1, 2, or 3; or $R^1$ and $R^2$ together form $-CH=CH-CH=CH-$ or methylenedioxy, when they are at the o-position to each other;

$R^3$ is hydrogen, $C_{1-8}$ alkyl, $C_{2-6}$ alkenyl, $C_{3-7}$ cycloalkyl, $C_{5-7}$ cycloalkenyl or

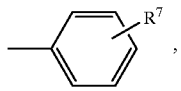

where $R^7$ is hydrogen, $C_{1-8}$ alkyl, $C_{1-8}$ alkoxy, $C_{1-3}$ alkylthio, chloro, bromo, fluoro, chloromethyl, trichloromethyl, trifluoromethyl, trifluoromethoxy, trichloromethoxy, difluoromethoxy, phenoxy, benzyloxy, hydroxy, trimethylsilyloxy, diphenyl-tert-butylsilyloxy or hydroxymethyl; or $C_{1-3}$ alky substituted by

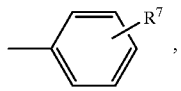

wherein $R^7$ is as defined above and zero, one or two $C_{1-3}$ alkyl;

Y is $-CH_2-$, $-CH_2CH_2-$, $-CH=CH-$, $-CH_2-CH=CH-$, $-CH=CH-CH_2-$, $-C(CH_3)=CH-$ or $-CH=C(CH_3)-$;

Z is $-Q-CH_2-W-CH_2-CO_2R^{12}$,

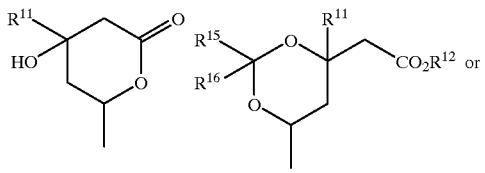

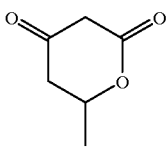

wherein Q is $-C(O)-$, $-C(OR^{13})_2-$ or $-CH(OH)-$,
W is $-C(O)-$, $-C(OR^{13})_2-$ or $-C(R^{11})(OH)-$,
$R^{11}$ is hydrogen or $C_{1-3}$ alkyl,
$R^{12}$ is hydrogen, alkyl of a chemically or physiologically hydrolyzable alkyl ester moiety, $NHR^{23}R^{24}R^{25}$, sodium, potassium or ½ calcium, where each of $R^{23}$, $R^{24}$ and $R^{25}$ is independently hydrogen or $C_{1-4}$ alkyl, each $R^{13}$ is independently a primary or secondary $C_{1-6}$ alkyl, or two $R^{13}$ together form $-(CH_2)_2-$ or $-(CH_2)_3-$, and each of $R^{15}$ and $R^{16}$ is independently a hydrogen atom or $C_{1-3}$ alkyl, or $R^{15}$ and $R^{16}$ together form $-(CH_2)_2-$ or $-(CH_2)_3-$.

9. The method of claim 6, wherein in the formula (Ia),
$R^3$ is hydrogen, methyl, ethyl, n-propyl, i-propyl, n-butyl, i-butyl, sec-butyl, tert-butyl, n-pentyl, i-pentyl, 1,2-dimethylpentyl, n-hexyl, n-heptyl, n-octyl, vinyl, n-propenyl, i-propenyl, 1-methyl-1-propenyl, 2-methyl-1-propenyl, 1,2-dimethyl-1-propenyl, c-propyl, c-butyl, c-hexyl, 1-methylcyclopropyl, 2-methylcyclopropyl, phenyl, 2-methylphenyl, 3-methylphenyl, 4-methylphenyl, 2-chlorophenyl, 3-chlorophenyl, 4-chlorophenyl, 2-methoxyphenyl, 3-methoxyphenyl, 4-methoxyphenyl, 3,4-dimethylphenyl, 3,4-dichlorophenyl, 3-trifluoromethylphenyl, benzyl, 4-chlorobenzyl, 4-methylbenzyl, 4-methoxybenzyl 2-phenethyl or 1-methylbenzyl;

when $R^{5a}$ and $R^{6a}$ are simultaneously hydrogen, $R^{4a}$ is hydrogen, 5-fluoro, 6-fluoro, 7-fluoro, 8-fluoro, 5-chloro, 6-chloro, 7-chloro, 8-chloro, 5-bromo, 6-bromo, 7-bromo, 8-bromo, 5-methyl, 6-methyl, 7-methyl, 8-methyl, 5-methoxy, 6-methoxy, 7-methoxy, 8-methoxy, 5-trifluoromethyl, 6-trifluoromethyl, 7-trifluoromethyl, 8-trifluoromethyl, 6-trisfluoromethoxy, 6-difluoromethoxy, 8-hydroxyethyl, 5-hydroxy, 6-hydroxy, 7-hydroxy, 8-hydroxy, 6-ethyl, 6-n-butyl or 7-dimethylamino; or when $R^{6a}$ is hydrogen, $R^{4a}$ and $R^{5a}$ together represent 6-chloro-8-methyl, 6-bromo-7-methoxy, 6-methyl-7-chloro, 6-chloro-8-hydroxy, 5-methyl-2-hydroxy, 6-methoxy-7-chloro, 6-chloro-7-methoxy, 6-hydroxy-7-chloro, 6-chloro-7-hydroxy, 6-chloro-8-bromo, 5-chloro-6-hydroxy, 6-bromo-8-chloro, 6-bromo-8-hydroxy, 5-methyl-8-chloro, 7-hydroxy-8-chloro, 6-bromo-8-hydroxy, 6-methoxy-7-methyl, 6-chloro-8-bromo, 6-methyl-8-bromo, 6,7-difluoro, 6,8-difluoro, 6,7-methylenedioxy, 6,8-dichloro, 5,8-dimethyl, 6,8-dimethyl, 6,7-dimethoxy, 6,7-diethoxy, 6,7-dibromo or 6,8-dibromo; or $R^{4a}$, $R^{5a}$ and $R^{6a}$ together represent, 5,7-dimethoxy-8-hydroxy, 5,8-dichloro-6-hydroxy, 6,7,8-trimethoxy, 6,7,8-trimethyl, 6,7,8-trichloro, 5-fluoro-6,8-dibromo or 5-chloro-6,8-dibromo.

10. The method of claim 7, herein in the formula (Ib),
$R^3$ is hydrogen, methyl, ethyl, n-propyl, i-propyl, n-butyl, i-butyl, sec-butyl, tert-butyl, n-pentyl, i-pentyl, 1,2-dimethylphenyl, n-hexyl, n-heptyl, n-octyl, vinyl, n-propenyl, i-propenyl, 1-methyl-1-propenyl, 2-methyl-1-propenyl, 1,2-dimethyl-1-propenyl, c-propyl, c-butyl, c-hexyl, 1-methylcyclopropyl, 2-methylcyclopropyl, phenyl, 2-methylphenyl, 3-methylphenyl, 4-methylphenyl, 2-chlorophenyl, 3-chlorophenyl, 4-chlorophenyl, 2-methoxyphenyl, 3-methoxyphenyl, 4-methoxyphenyl, 3,4-dimethylphenyl, 3,4-dichlorophenyl, 3-trifluoromethylphenyl, benzyl, 4-chlorobenzyl, 4-methylbenzyl, 4-methoxybenzyl, 2-phenethyl or 1-methylbenzyl;

$R^{4b}$ is hydrogen, methyl, ethyl, n-propyl, i-propyl, n-butyl, i-butyl, sec-butyl, tert-butyl, cyclopropyl, cyclohexyl, phenyl, 2-, 3- or 4-fluorophenyl, 2-, 3-, or 4-chlorophenyl, 2-, 3-, or 4-tolyl, 2- 3- or 4-methoxyphenyl, 2-, 3- or 4-trifluoromethylphenyl, 2-, 3-, 4-chloromethylphenyl, 3- or 4-ethoxyphenyl, 4-(2-methylbutyl)phenyl, 4-n-heptylphenyl, 4-n-octylphenyl, 4-n-pentylphenyl, 4-n-hexylphenyl, 4-n-propylphenyl, 4-n-butylphenyl, 4-tert-butylphenyl, 4-n-butoxyphenyl,4-n-pentyloxyphenyl, 4-n-hexyloxyphenyl, 4-n-heptyloxyphenyl, 4-n-octyloxyphenyl, 4-phenoxyphenyl, 4-biphenyl, 4-trichloromethoxyphenyl, 2,4-difluorophenyl, 2,6-difluorophenyl, 2,3-difluorophenyl, 3,5-difluorophenyl, 2,5-difluorophenyl, 3,4-difluorophenyl, 2,4-dichlorophenyl, 2,6-dichlorophenyl, 2,3-dichlorophenyl, 2,5-dichlorophenyl, 3,5-dichlorophenyl, 3,4-dichlorophenyl, 2,3-dimethylphenyl, 2,5-dimethylphenyl, 2,6-dimethylphenyl, 3,4-dimethylphenyl, 2,5-dimethoxyphenyl, 2,6-dimethoxyphenyl, 2,4-dimethoxyphenyl, 3,4-dimethoxyphenyl, 3,5-dimethoxyphenyl, 3,5-bis(trifluoromethyl)phenyl, 3,4-methylenedioxyphenyl, 2,4,6-trimethoxyphenyl, 3,4,5-trimethylphenyl or 2,4,6-triisopropylphenyl;

$R^{5b}$ is a group bonded to the nitrogen atom at the 1-position of the pyrazolopyridine ring and is methyl, ethyl, n-propyl, i-propyl, n-butyl, i-butyl, sec-butyl, tert-butyl, 2,2,2-trifluoroethyl, 2-hydroxyethyl, cyclohexyl, benzyl, 2-chlorobenzyl, 2-hydroxybenzyl, 3-trifluoromethylbenzyl, 2-phenylethyl, phenyl, 2-, 3- or 4-chlorophenyl, 2-, 3- or 4-bromophenyl, 2-, 3- or 4-fluorophenyl, 2-, 3- or 4-tolyl, 2-, 3- or 4-trifluoromethylphenyl, 3-or 4-methoxyphenyl, 2-hydroxyphenyl, 4-isopropylphenyl, 4-tert-butylphenyl, 4-trifluoromethoxyphenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,6-trichlorophenyl, 2,3,4-trichlorophenyl, 2,4-difluorophenyl, 3,5-bis(trifluoromethyl)phenyl, 3-chloro-4-tolyl, 3-chloro-6-tolyl, 4-chloro-2-tolyl, 2-chloro-6-tolyl, 2-chloro-6-fluorophenyl, 2-chloro-5-trifluoromethylphenyl, 3-chloro-4-fluorophenyl, 4-bromo-3-chlorophenyl, 2-chloro-4-trifluoromethylphenyl, 3-fluoro-6-tolyl, a-naphthyl; 2-pyridyl, 3-methyl-5-trifluoromethyl-2-pyridyl, 4-pyridyl or 2,6-dichloro-4-pyridyl.

11. A method of claim 8, wherein in the formula (Ic), $R^3$ is hydrogen, methyl, ethyl, n-propyl, i-propyl, n-butyl, i-butyl, sec-butyl, tert-butyl, n-pentyl, i-pentyl, 1,2-dimethylpentyl, n-hexyl, n-heptyl, n-octyl, vinyl, n-propenyl, i-propenyl, 1-methyl-1-propenyl, 2-methyl-1-propenyl, 1,2-dimethyl-1-propenyl, c-propyl, c-butyl, c-hexyl, 1-methylcyclopropyl, 2-methylcyclopropyl, phenyl, 2-methylphenyl, 3-methylphenyl, 4-methylphenyl, 2-chlorophenyl, 3-chlorophenyl, 4-chlorophenyl, 2-methoxyphenyl, 3-methoxyphenyl, 4-methoxyphenyl, 3,4-dimethylphenyl, 3,4-dichlorophenyl, 3-trifluoromethylphenyl, benzyl, 4-chlorobenzyl, 4-methylbenzyl, 4-methoxybenzyl, 2-phenethyl or 1-methylbenzyl;

each of $R^{4c}$ and $R^{5c}$, which are independent of each other, is hydrogen, methyl, ethyl, n-propyl, i-propyl n-butyl, i-butyl, sec-butyl, tert-butyl, n-pentyl, 1,2-dimethylpentyl, n-hexyl, n-heptyl, n-octyl, cyclopropyl, cyclobutyl, cyclopentyl, cyclohexyl, 2-methylcyclohexyl, cycloheptyl, cyclopropylmethyl, vinyl, 1-methylvinyl, 1-propenyl, allyl, 1-methyl-1-propenyl, 1-methyl-2-propenyl, 2-methyl-2-propenyl, 2-butenyl, 1-ethylvinyl, 1,2-dimethyl-1-propenyl, 1,2-dimethyl-2-propenyl, 1-ethyl-1-propenyl, 1-ethyl-2-propenyl, 1-methyl-1-butenyl, 1-methyl-2-butenyl, 2-methyl-1-butenyl, 1-i-polyvinyl, 1-methyl-1-pentenyl or phenyl; or $R^{4c}$ and $R^{5c}$ together form ethylene, trimethylene, tetramethylene, pentamethylene, methyltetramethylene, chlorotetramethylene or phenyltetramethylene.

12. The method of claim 6, wherein said compound is (E)-3,5-dihydroxy-7-[4'-(4"-fluorophenyl)-2'-cyclopropyl-quinolin-3'-yl]hept-6-enoic acid, a compound having such carboxylic acid condensed with hydroxy at the 5-position to form a lactone, a sodium or calcium salt of such carboxylic acid, or a $C_{1-3}$ alkyl ester of such carboxylic acid.

13. The method of claim 7, wherein said compound is (E)-3,5-dihydroxy-7-[6'-cyclopropyl-4'-(4"-fluorophenyl)-1',3'-dimethylpyrazolo[3,4-b]pyridin-5'-yl]hept-6-enoic acid, a compound having such carboxylic acid condensed with hydroxy at the 5-position to form a lactone, a sodium or calcium salt of such carboxylic acid, or a $C_{1-3}$ alkyl ester of such carboxylic acid.

14. The method of claim 8, wherein said compound is (E)-3,5-dihydroxy-7-[6'-cyclopropyl-3'-ethyl-4'-(4"-fluorophenyl)-2'-methylthieno[2,3-b]pyridin-5'-yi]hept-6-enoic acid, a compound having such carboxylic acid condensed with hydroxy at the 5-position to form lactone, a sodium or calcium salt of such carboxylic acid, or a $C_{1-3}$ alkyl ester of such carboxylic acid.

* * * * *